United States Patent
Yamashita

(10) Patent No.: US 8,821,909 B2
(45) Date of Patent: *Sep. 2, 2014

(54) METHODS FOR TREATING A PLANT EXPOSED TO A PHYTOTOXICANT

(75) Inventor: Thomas T. Yamashita, Turlock, CA (US)

(73) Assignee: Thomas T. Yamashita, Turlock, CA (US)

( * ) Notice: Subject to any disclaimer, the term of this patent is extended or adjusted under 35 U.S.C. 154(b) by 323 days.

This patent is subject to a terminal disclaimer.

(21) Appl. No.: 12/846,521

(22) Filed: Jul. 29, 2010

(65) Prior Publication Data

US 2011/0020281 A1  Jan. 27, 2011

Related U.S. Application Data

(63) Continuation of application No. 10/794,187, filed on Mar. 4, 2004, now Pat. No. 7,906,129.

(51) Int. Cl.
*A01N 25/00* (2006.01)
*C12M 1/00* (2006.01)

(52) U.S. Cl.
USPC .................. 424/405; 435/283.1; 435/975

(58) Field of Classification Search
CPC .......... C05F 11/00; C05F 11/10; C05F 5/006; C05F 11/08; C05F 7/02; C05F 11/02; C05F 5/008; A01N 37/40; A01N 2300/00; A01N 63/04; A01N 25/30; A01N 43/16; A01N 63/00; A01N 63/02; A01N 41/04; A01N 61/00; A01N 65/00
See application file for complete search history.

(56) References Cited

U.S. PATENT DOCUMENTS

| | | | |
|---|---|---|---|
| 2,637,645 A | 5/1953 | Tischler et al. | |
| 5,549,729 A | 8/1996 | Yamashita | |
| 5,582,627 A | 12/1996 | Yamashita | |
| 5,696,094 A | 12/1997 | Yamashita | |
| 5,797,976 A | 8/1998 | Yamashita | |
| 6,121,195 A * | 9/2000 | Nonomura et al. | 504/136 |
| 6,165,245 A | 12/2000 | Yamashita | |
| 6,187,326 B1 | 2/2001 | Yamashita | |
| 6,309,440 B1 | 10/2001 | Yamashita | |
| 6,318,023 B1 | 11/2001 | Yamashita | |
| 6,336,772 B1 | 1/2002 | Yamashita | |
| 6,383,245 B1 | 5/2002 | Yamashita | |
| 6,475,258 B1 | 11/2002 | Yamashita | |
| 6,524,600 B2 | 2/2003 | Yamashita | |
| 6,874,277 B2 * | 4/2005 | Yamashita | 47/58.1 SC |
| 6,953,585 B2 | 10/2005 | Yamashita | |
| 7,906,129 B2 * | 3/2011 | Yamashita | 424/405 |
| 7,927,616 B2 * | 4/2011 | Yamashita | 424/406 |
| 2001/0000325 A1 | 4/2001 | Yamashita | |

* cited by examiner

*Primary Examiner* — Debbie K Ware
(74) *Attorney, Agent, or Firm* — Bret E. Field; Bozicevic, Field & Francis LLP

(57) ABSTRACT

Methods of treating a plant exposed to a phytotoxicant are provided. Embodiments of the subject methods include identifying a plant exposed to a phytotoxicant and applying an assimilable carbon-skeleton energy component-comprising composition to the identified plant. Embodiments of the subject compositions may include one or more of a macronutrient component, micronutrient component, vitamin/cofactor component, complexing agent and microbe. Kits for use in practicing the subject invention are also provided. The subject methods find use in a variety of different applications in which a plant is phytotoxic or at least in danger of becoming phytotoxic due to exposure or potential exposure to a phytotoxicant.

22 Claims, 3 Drawing Sheets

FIG. 1A

| Common Name | Trade Name | Chemical Name | Category | Scenario(s) |
|---|---|---|---|---|
| Glyphosate | Roundup | N(phosphonomethyl) glycine | Phosphono Amino Acid Herbicide | Drift, Spray, Soil |
| Chlorothal | Dacthal | Dimethyl tetrachloroterephthalate | Phthalic Acid Herbicide | Drift, Spray, Soil |
| Norflurazon | Solicam | 4-chloro-5-(methylamino)-2-[3-(trifluoromethyl)phenyl]-3(2H)-pyridazinone | Pyridazinone Herbicide | Drift, Spray, Soil |
| Oxadiazon | Ronstar | 2-tert-butyl-4-(2,4-dicloro-5-isoproproxy-phenyl)1,3,4-oxadiasolin-5-one | Pyridinone Herbicide | Drift, Spray, Soil |
| Picloram | Tordon | 4-amino-3,5,6-trichloropicolinic acid | Picolinic Acid Herbicide | Drift, Spray, Soil |
| Clopyralid | Lontrel | 3,6-ichloro-2-pyridinecarboxylic acid | Pyridinoxy Acid Herbicide | Drift, Spray, Soil |
| Chlorsulfuron | Glean | 2-chloro-N-[[(4-methyoxy-6-methyl-1,3,5-triazin-2-yl)aminocarbonyl]-benzenesulfonamide | Sulfonylurea Herbicide | Drift, Spray, Soil |
| Sulfometuron-Methyl | Oust | 2-[[[[(4,6-dimethyl-2-pyrimidinyl)amino]carbonyl]amino]sulfon yl]benzoic acid | Sulfonylurea Herbicide | Drift, Spray, Soil |
| Cycloate | Ro-Neet | S-ethylcyclohexylethylthiocarbamate | Thiocarbamate Herbicide | Drift, Spray, Soil |
| Simazine | Princep | 2-chloro-4,6-bis(ethylamino)-s-triazine | Triazine Herb | Drift, Spray, Soil |
| Metribuzin | Sencor | 4-amino-6-(1,1-dimethyl)-3-(methylthio)-1,2,4-triazin-5(4H)-one | Triazine Herb | Drift, Spray, Soil |
| Bromacil | Hyvar | 5-bromo-3-sec-butyl-6-methyluracil [5-bromo-6-methyl-3-(1-methylpropyl)uracil | Uracil Herb | Drift, Spray, Soil |
| Metolachlor | Dual | 2-chloro-N-(2-ethyl-6-methylphenyl)-N-(2-methoxy-1-methylethyl)acetamide | Acetanilide Herb | Drift, Spray, Soil |
| Napropamide | Devrinol | 2-(alpha-naphthoxy)-N,N-diethylpropionamide | Substituted Amide Herb | Drift, Spray, Soil |
| Pronamide | Kerb | 3,5-dichloro(N-1,1-dimethyl-2-propynyl)benzamide | Substituted Amide Herb | Drift, Spray, Soil |
| MSMA | MSMA | Monosodium Methanearsonate | Arsenical Herb | Drift, Spray, Soil |
| Dicamba | Banvel | 2-methoxy-3,6-dichlorobenzoic acid | Benzoic Acid Herb | Drift, Spray, Soil |
| Bromoxynil | Buctril | 3,5-dibromo-4-hydroxybenzonitrile | Substituted Nitrile Herb | Drift, Spray, Soil |

FIG. 1B

| Common Name | Trade Name | Chemical Name | Category | Scenario(s) |
|---|---|---|---|---|
| Bentazon | Basagran | 3-(1-methylethyl)-1H-2,1,3-benzothiadizin-4(3H)-one 2,2-dioxide | Benzothiadiazole Herb | Drift, Spray, Soil |
| Paraquat | Paraquat | 1,1'-dimethyl-4,4'-bipyridylium ion (dichloride) | Bipyridylium Herb | Drift, Spray |
| Trifluralin | Treflan | alpha, alpha, alpha-trifluoro-2,6-dinitro-N,N-dipropyl-p-toluidine | Dinitroaniline Herb | Drift, Spray, Soil |
| Oxyfluorfen | Goal | 2-chloro-1(3-ethoxy-4-nitrophenoxy)-4-(trifluoromethyl)benzene | Diphenyl Ether Herb | Drift, Spray, Soil |
| Imazamethabenz-methyl | Assert | m-toluic acid, 6-(4-isopropyl-4-methyl-5-oxo-2-imidazolin-2-yl-methyl ester and 2-(4-isopropyl-4-methyl-5-oxo-2-imidazolin-2-yl, methyl ester | Imidazolinone Herb | Drift, Spray, Soil |
| 2,4-D | 2,4-D | (2,4-dixhlorophenoxy)acetic acid | Phenoxy Acid Herb | Drift, Spray, Soil |
| Diuron | Krovar | 3-(3,4-dichlorophenyl)-1,1-dimethylurea | Phenylurea Herb | Drift, Spray, Soil |
| Sulfur | Thiolux, Microthiol, Others | Various forms of inorganic sulfur | Inorganic Fungicide, Miticide, Insecticide | Drift, Spray; Alone &/or mixed w/incompatible reactants (e.g. oil) |
| Copper | Kocide, COCS, Others | Various forms of inorganic copper | Inorganic Microbialcide | Drift, Spray, Soil; Alone &/or mixed w/incompatible reactants (e.g. phosphorous acid) |
| Organic Fungicides Containing Sulfur | Dithane, Thiram, Captan, Plantvax, Others | Various forms of organic fungicides containing sulfur | Organic Fungicides | Drift, Spray, Alone &/or mixed w/incompatible reactants (e.g. oil or oil-containing spreaders) |

FIG. 1C

| Common Name | Trade Name | Chemical Name | Category | Scenario(s) |
|---|---|---|---|---|
| Organic Insecticides &/or Miticides Containing Sulfur | Malathion, Cygon, Di-Syston, Orthene, Curacron, Diazinon, Lorsban, Imidan, Omite, Vydate, Lannate, Others | Various forms of organic insecticides &/or miticides containing sulfur | Organic Insecticides &/or Miticides | Drift, Spray; Alone &/or mixed w/incompatible reactants (e.g. oil or oil-containing spreaders) |
| Hydrgen Cyanamide | Dormex | Hydrogen Cyanamide | Herbicide, Promotion of Budbreak, Thinning Agent | Drift, Spray |
| Organosilicones | Silwet, Kinetic, Penewet, Si-100, Break-Thru, Others | Polyalkyleneoxide and Polydimethylsiloxane blend | Nonionic Surfactant | Drift, Spray; can aggravate toxicity, esp when used in hot weather |
| Crop Oil & Surfactants Containing Oil | Agri-Dex, Inhance, Prime Oil, R900, Others | Various forms of oil &/or surfactants containing oil | Surfactants, Spreaders, Extenders, Penetrators | Drift, Spray; Alone &/or mixed w/incompatible reactants; esp enhanced in toxicity in hot weather |
| Allelopathic Chemicals | Juglone, Hydroxamic Acid, Eucalyptol, Others | Acids, Aldehydes, Cyanogenic Glycosides, Thiocyanates, Lactones, Coumarins, Quinones, Flavanoids, Tannins, Alkaloids, Terpenoids, Steroids, Others | Allelopathic Chemicals | Generally via soil; Previous crops' exudates and by-products, which hinder subsequent growth |

METHODS FOR TREATING A PLANT EXPOSED TO A PHYTOTOXICANT

CROSS REFERENCE TO RELATED APPLICATION

This application is a continuation of application Ser. No. 10/794,187, filed Mar. 4, 2004, now U.S. Pat. No. 7,906,129.

FIELD OF THE INVENTION

The field of this invention is agriculture.

BACKGROUND OF THE INVENTION

Many pesticides (e.g., insecticides, herbicides, bactericides, fungicides, etc.) and other substances, impart phytotoxic responses, i.e., subtle to distinct hindrances to the physiological functions, to plants. Such substances that result in phytotoxicity may generally be referred to as phytotoxicants.

Phytotoxicity resulting from a variety of sources and scenarios plague the agricultural industry. For example, plant toxicities may result from accidental drift of a pesticide onto a plant, accidental spraying of a plant with a toxicant, planting into soil that has been contaminated with a toxicant, and the like.

Regardless of the source or scenario by which a phytotoxicant is contacted with a plant, phytotoxicity can have severe adverse consequences, including serious economic consequences, to both the affected plant and the grower. For example, phytotoxicity may result in crop losses, forced removal and replanting of crops, plant death and in certain instances may render the soil unusable for crops for prolonged periods of time.

Accordingly, there continues to be an interest in the development of methods that at least mollify the effects of a phytotoxicant on an exposed plant, regardless of the source of the phytotoxicant or scenario by which the plant has been exposed to the phytotoxicant.

SUMMARY OF THE INVENTION

Methods of treating a plant exposed to a phytotoxicant are provided. Embodiments of the subject methods include identifying a plant exposed to a phytotoxicant and applying an assimilable carbon-skeleton energy component-comprising composition to the identified plant. Embodiments of the subject compositions may include one or more of a macronutrient component, micronutrient component, vitamin/cofactor component, complexing agent and microbe. Kits for use in practicing the subject invention are also provided. The subject methods find use in a variety of different applications in which a plant is phytotoxic or at least in danger of becoming phytotoxic due to exposure or potential exposure to a phytotoxicant.

BRIEF DESCRIPTIONS OF THE DRAWINGS

FIGS. 1A-1C 1 show exemplary phytotoxicants that may be exposed to a plant resulting in phytotoxicity of the plant- which phytotoxicity may be treated in accordance with the subject methods.

DETAILED DESCRIPTION OF THE INVENTION

Methods of treating a plant exposed to a phytotoxicant are provided. Embodiments of the subject methods include identifying a plant exposed to a phytotoxicant and applying an assimilable carbon-skeleton energy component-comprising composition to the identified plant. Embodiments of the subject compositions may include one or more of a macronutrient component, micronutrient component, vitamin/cofactor component, complexing agent and microbe. Kits for use in practicing the subject invention are also provided. The subject methods find use in a variety of different applications in which a plant is phytotoxic or at least in danger of becoming phytotoxic due to exposure or potential exposure to a phytotoxicant.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

As summarized above, the subject invention provides methods for treating a plant identified as being exposed to a phytotoxicant. The subject methods may be employed to at least reduce or mollify, and in certain instances prevent, phytotoxicity of a plant brought about by the exposure of a phytotoxicant-inducing substance (i.e., a phytotoxicant) to the plant. The subject methods may be employed to mollify or "buffer" the magnitude of, and in certain instances eliminate, phytotoxicity.

Phytotoxicity may be characterized broadly as plant injury and may manifest or express itself in a number of ways including subtle and/or obvious symptoms. For example, symptoms may include compromised physical and/or physiological activity or function of one or more aspects of a plant and may range from minor leaf speckling to plant death. Phytotoxicity symptoms may include, but are not limited to, chlorosis, necrosis, burning, leaf speckling or banding, leaf drop, fruit spotting, distortion of new growth, stunting of growth, cessation of growth, discoloration (e.g., yellowing of the leaves (soaps)), root injury (e.g., poor root development or growth), puckering (xylene injury), tip browning, plant death, and the like. For example, phytotoxicity may result in a reduction or compromise in a plant's metabolic activity, such as manifested as adversely affecting (e.g., stunting) plant growth, e.g., phytotoxicity may be observed as an adverse effect on a plant's overall vigor and growth.

A plant may be exposed to a phytotoxicant in a number of different ways and it is to be understood that the subject methods are not limited to any particular exposure or contacting method or particular phytotoxicant. For example, exposure of a plant with a phytotoxicant may be purposeful or accidental and may be direct (e.g., directly contacted to at least a portion of a plant such as the foliage of a plant or the like), or indirect (e.g., contacted via contaminated soil or water). Accordingly, the subject methods may be employed to at least reduce phytotoxicity of a plant exposed to a phytotoxicant, where the exposure may be accomplished by any method, including, but not limited to, drift onto the plant of a phytotoxicant, accidental foliar spray with a phytotoxicant, purposeful foliar spray with a phytotoxicant, accidental foliar spray with a reactant that negatively interacts with a previously applied substance to produce a phytotoxic effect, purposeful foliar spray with a reactant that negatively interacts with a previously applied substance to produce a phytotoxic effect, planting in phytotoxicant-contaminated soil, irrigating with phytotoxicant-contaminated water, pollution, and the like. For example, phytotoxicity may result from the application of substance such as a pesticide that is otherwise safe, but which causes phytotoxicity if applied at an excessive rate. For example, in such as instance exposure may be purposeful, but the amount or rate of the phytotoxicant used may result in phytotoxicity of the exposed plant. Phytotoxicity may also be caused by mixing too many pesticides together, e.g., in a spray tank, all at proper and safe rates if applied separately and which separated applications may not cause phytotoxicity, but when mixed together may cause phytotoxicity. Phytotoxicity may also occur from the build-up of successive pesticide application wherein the individual applications are not phytotoxic, but phytotoxicity may occur via build-up from regular applications of the same type of a pesticide, e.g., applied too many times in succession and/or at too close an interval. Phytotoxicity may occur due to an interaction between two substances. For example, a pesticide may be applied to a plant without injury, but when mixed with one or more incompatible substances (e.g., mixed prior to or after application to a plant (may already be in the soil or on the plant)), may result in phytotoxicity. Phytotoxicity may also be "episodic" which refers to an episode wherein a common pesticide, for reasons that may or may not be known, suddenly causes plant injury, which may never have occurred before in prior applications. In many instances this type of episodic phytotoxicity may occur due to factors such as weather. For example, some pesticides are safe in cooler weather whereas they can become phytotoxicants in high heat conditions. Water-stressed plants can also be very sensitive to otherwise safe pesticide applications. Improper cleaning of the spray tank from a previous application may also cause episodic phytotoxicity.

The term "phytotoxicant" is used herein broadly to refer to any substance, organic or inorganic, that may injure or damage a plant, i.e., the application of which may result in phytotoxicity to a plant as described above. Phytotoxicants as used herein include phytotoxicants known, suspected, not known or not suspected, of resulting in phytotoxicity of a plant when contacted thereto. Substances that are potential phytotoxicants are also encompassed by the subject methods. Accordingly, phytotoxicants may include, but are not limited to, pesticides, pests, pathogens, and the like.

The term "pesticide" is meant broadly to include any agent that affects the mortality, morbidity or behavior of a target organism and includes, but is not limited to, insecticides, acaracides, miticides, fungicides, bactericides, herbicides, antibiotics, antimicrobials, nemacides, rodenticides, entomopathogens, phermones, attractants, plant growth regulators, insect growth regulators, chemosterilants, repellents, viruses and phagostimulents. Examples of these pesticides are known to those skilled in the art, and many are readily commercially available. Pesticides may be in any form, e.g., may be in solid or liquid form, may be an organic pesticide, may be an inorganic pesticide, and the like. Pesticides may be synthetic or man-made. Pesticides may be a naturally occurring, derived from natural materials or may be non-naturally occurring. A plant may be exposed to a single pesticide or a plurality of pesticides, where one or more may result in phytotoxicity. As noted above, pesticides as used in the context of the subject invention may be known to be phytotoxic or may be at least suspected of being phytotoxic, or may not be known or even suspected of being phytotoxic.

FIGS. 1A-1C provide exemplary pesticides, the contact of which to a plant may result in phytotoxicity. However, such is for exemplary purposes only and is in no way intended to limit the scope of the invention.

Embodiments of the subject methods include contacting a plant that has been exposed, or is at least suspected of being exposed, to a phytotoxicant with composition that is capable of at least reducing the phytotoxicity and in certain instances is capable of completely eliminating the phytotoxicity (i.e., capable of complete detoxification of a plant). While the subject methods are described primarily with reference to applying the subject compositions to a plant that has already been contacted with a phytotoxicant, the subject compositions may be employed prophylactically to a plant, e.g., before a plant is contacted with a phytotoxicant or before it is known that a substance is a phytotoxicant.

Accordingly, embodiments include identifying a plant that has been exposed, or at least is suspected of being exposed, to a phytotoxicant. Identifying a plant that has been exposed or is at least suspected of being to a phytotoxicant may be accomplished in any suitable manner. Identification of a plant that has been exposed or is at least suspected of being exposed to a phytotoxicant may be accomplished using qualitative and/or quantitative methods. For example, such identification may be highly accurate and/or quantitative, or may not be so highly accurate and may include estimating or even guessing whether a plant has been exposed to a phytotoxicant. Accordingly, identifying a plant that has been exposed or is at least suspected of being exposed to a phytotoxicant is used broadly herein to include any method or process for identifying, determining or evaluating, i.e., assessing or measuring, or otherwise arriving at a qualitative and/or quantitative determination of whether a plant has been, or is suspected being, exposed to a phytotoxicant. As such, by identify a plant in this context is meant to include qualitative and quantitative determinations including arriving at a conclusion that it is unknown whether a plant has been exposed to a phytotoxicant. The identification of a plant that has been exposed or is at least suspected of being exposed to a phytotoxicant may be accomplished empirically (i.e., determined by experiment or observation) or may be determined from deduction, hypothesis, theory, e.g., solely or in part from theory or prior knowledge.

Methods that may be employed include, but are not limited to, assaying ground water, plant tissue, and the like, for evidence of a phytotoxicant and/or phytotoxicity. Observing the physical and/or physiological activity or function of one or more aspects of a plant may be employed and may include observing plant death, chlorosis, necrosis, burning, leaf speckling or banding, leaf drop, fruit spotting, distortion of new growth, stunting of growth, cessation of growth, discoloration (e.g., yellowing of the leaves (soaps)), root injury (e.g., poor root development or growth), puckering (xylene injury), tip browning, a reduction or compromise in a plant's metabolic activity such as manifested as adversely affecting (e.g., stunting) plant growth, a plant's overall vigor and growth, etc. In certain embodiments a *Lemna* growth assay may be used in testing the phytotoxicity of pesticides and other environmental chemicals to higher plants. For example, *Lemna* species can easily be used for the examination of pesticide exposure through water, for the study of pesticide drift and research into the effects of surface films at the air-water interface (see, e.g., Swanson 1989, Taraldesen and Norberg-King 1990). References of interest include: US EPA. 1996b. Ecological Effects Test Guidelines. OPPTS 850.4400 Aquatic Plant Toxicity Test Using *Lemna* spp., Tiers I and II. EPA 712-C-96-156; Lockhart, L. W., B. N. Billeck and C. L. Baron. 1989. "Bioassays with a floating aquatic plant (*Lemna minor*) for effects of sprayed and dissolved glyphosate." Hydrobiologia. 188/189: 353-359; and "*A Sediment Toxicity Method Using Lemna Minor, Duckweed*" a poster presentation (Society of Environmental Toxicology and Analytical Chemistry meeting, Nashville, Tenn., November, 2000) by Lazorchak, J. M., Williams, D. E., Suszcynsky-Meister, E. M. and Smith, M. E., U.S. EPA and SBI Environmental, Cincinnati, Ohio.

As noted above, in certain embodiments the determination of whether a plant has been exposed or is at least suspected of being exposed to a phytotoxicant may be based in whole or in part on prior knowledge and include educated guesses, speculation, etc, and in certain embodiments the determination of whether a plant has been contacted with a phytotoxicant may be determined to be unknown. In certain embodiments, such a determination may be based in whole or in part on the knowledge of pesticide application in an area surrounding a plant, e.g., applied to surrounding crops.

Once it is determined that a plant is phytotoxic or is at risk if becoming phytotoxic, e.g., has been identified as being exposed or suspected of being exposed to a phytotoxicant or potential phytotoxicant, a composition for combating (e.g., at least reducing, eliminating or preventing) phytotoxicity may be applied to the plant in a manner effective to treat the plant for phytotoxicity. By "treat" is meant that at least an amelioration of the symptoms associated with the phytotoxicant afflicting the plant is achieved, where amelioration is used in a broad sense to refer to at least a reduction in the magnitude of a parameter, e.g., symptom, associated with the plant being treated. As such, treatment of a plant includes situations where the phytotoxicant, or at least symptoms associated the phytotoxicant, are completely inhibited, e.g. prevented-from happening, or stopped, e.g. terminated eliminated, such that the plant no longer suffers from the effects of the phytotoxicant, or at least the symptoms that characterize the phytotoxicant.

The practice of the subject methods may result in one or more of: partial or complete detoxification, recovery of normal physiological functions, inciting enhanced production of membrane tissues and concomitant production of enzymes needed for efficient physiological functions, de novo synthesis of toxicant degradative enzymes, and the like. In certain embodiments the subject compositions may impart a degree of preventive phytotoxicant tolerance to a treated plant As noted above, to treat a plant for phytotoxicity, the subject methods include applying a phytotoxicity-fighting composition to the plant. Embodiments of the subject compositions are assimilable carbon skeleton energy component-containing compositions and as such include an assimilable carbon skeleton energy component. Other components for combating phytotoxicity also be included in the subject compositions and include, but are not limited to, one or more micronutrients component, a macronutrient component, a vitamin/cofactor component, a complexing agent and a beneficial microbial inoculant.

The inventor of the subject invention has discovered that the subject compositions (i.e., compositions that include one or more of: an assimilable carbon skeleton energy component, a macronutrient component, a micronutrient component, a vitamin/cofactor component, a complexing agent and at least one microbial species) provide unexpected, beneficial results when administered to a plant suffering from phytotoxicity. More specifically, the inventor of the subject invention has realized that, when applied to a phytotoxicant-exposed plant, the subject compositions provide subtle to significant protection from the effects of phytotoxicant-induced phytotoxicity, where in certain instances phytotoxic effects may be completely prevented or eliminated.

Specifically, the inventor of the subject invention has discovered that the magnitude or degree of phytotoxcity may at least be reduced in a plant by employing the subject methods and in certain instances phytotoxicity may be completely eliminated. For example, in certain embodiments the magnitude of phytotoxicity, as measured by visual observation of degree of symptom mitigation and/or chemical laboratory analysis for the toxicant, such as, but not limited to, visual assessment of the degree of mitigation of one or more of (a) tissue distortion, (b) color alteration, (c) level of stunting, (d) recovery from necrosis, (e) aborting of flowers and/or fruit, (f) extent of overall growth, (g) leaf size and/or density, and the like. In certain embodiments, the magnitude of phytotoxicity may be decreased from about 5% to about 100%, e.g., from about 25% to about 100%, e.g., from about 50% to about 100%.

Accordingly, the inventor of the subject invention has discovered that the application of the subject methods to a plant suffering from phytotoxicity provides at least a reduction in one or more aspects of the results of phytotoxicity and/or a reduction in the phytotoxicant in the soil and/or affected tissues, where phytotoxicity may be characterized as described above, i.e., broadly as plant injury brought about by the exposure to a phytotoxicant. A decrease in phytotoxicity magnitude or severity by employing the subject methods may be observed as at least an amelioration of the phytotoxic symptoms associated with the plant, where amelioration is used in a broad sense to refer to at least a reduction in the magnitude of a parameter, e.g., symptom, associated with the plant being treated. Accordingly, at least a reduction in the magnitude (typically within the ranges provided above) of one or more symptoms may be provided by the practice of the subject invention, where such symptoms include, but are not limited to one or more of: chlorosis, necrosis, burning, leaf speckling or banding, leaf drop, fruit spotting, distortion of new growth, stunting of growth, cessation of growth, discoloration (e.g., yellowing of the leaves (soaps)), root injury (e.g., poor root development or growth), puckering (xylene injury), tip browning, plant death, reduction or compromise in a plant's metabolic activity such as manifested in a plant's growth, reduction in overall vigor and growth, and the like.

The components of the subject compositions are now described in greater detail. It is to understood that one or more, including all, of the components may be employed in a phytotoxicity-fighting composition.

Assimilable Carbon Energy Component

Embodiments of the subject compositions also include an assimilable carbon skeleton energy (ACSE) component. ACSE components that find use in the subject compositions are carbon-containing substances which provide a readily plant-assimilable source of both carbon and energy for the plant. Accordingly, the function of this component is to supply carbon skeleton for synthesis of proteins and other plant molecules and to supply energy for plant metabolism such that an ACSE component, when suitably assimilated or absorbed by the plant, may provide a source of energy and also a source of carbon skeleton from which, for example, proteins may be synthesized by the plant. As the carbon skeleton energy components are assimilable by a plant, they are water soluble components so as to be easily assimilable by a plant.

Embodiments include an ACSE component that is a $C_2$ to $C_{14}$, e.g., $C_4$ to $C_8$ compound or polymer thereof, e.g., a polymer in which the monomeric units are $C_2$ to $C_{14}$ compounds, such as a polysaccharide. The ACSE component may be a single carbon containing compound or a composition of two or more different carbon containing or organic compounds. Compounds and compositions capable of serving as a ACSE component include, but are not limited to: complex organic compositions, such as molasses (e.g. cane, sugar beet, sorghum, etc.), whey, corn steep liquor, grape syrup, maple syrup, corn syrup, etc; sugars, e.g. sucrose, fructose, glucose, lactose, galactose, dextrose, maltose, raffinose, ribose, ribulose, xylulose, xylose, amylose, arabinose, etc.; sugar phosphates, e.g. fucose-P, galactose-P, glucose-P, lactose-P, maltose-P, mannose-P, ribose-P, ribulose-P, xylose-P, xylulose-P, etc.; sugar alcohols, e.g. adonitol, sorbitol, mannitol, maltitol, ribitol, galactitol, glucitol, etc.; organic acids, e.g. gluccuronic acid, alpha ketoglutaric acid, galactonic acid, glucaric acid, gluconic acid, pyruvic acid, polygalacturonic acid, citric acid, succinic acid, malic acid, isocitric acid, folic acid, etc.; nucleotides and bases, e.g. adenosine, adenosine-P, uridine, uridine-P, thymine, thymine-P, cytosine, cytosine-P, guanine, guanine-P, etc.; and amino acids, e.g. glycine, alanine, leucine, isoleucine, asparagine, tyrosine, phenylalanine, serine, cysteine, valine, proline, methionine, glutamine, threonine, lysine, aspartic acid, glutamic acid, arginine, and the like.

Of interest are sucrose ACSE components and corn syrup ACSE components. Also of interest is molasses. For example, in those embodiments that employ molasses, the molasses may be obtained from a number of commercial sources, including cane molasses, etc., where commercial sources of molasses include: Westway Terminal, Stockton Calif.; PM Ag, Stockton, Calif.; and the like.

The ACSE component of the subject compositions are present in an amount suitable to at least reduce the phytotoxic effects of a phytotoxicant contacted with a plant, where the ACSE component may provide for at least reduced phytotoxicity alone or may function in combination with other components in a composition. Accordingly, embodiments include an amount of ACSE component present in a subject composition in at least a phytotoxicity-reducing amount, i.e., in at least an amount sufficient to at least reduce phytotoxicity. The particular amount of a given ACSE component present in a given composition depends on a variety of factors such as the particular plant to which the composition is to be administered, the particular ACSE component employed, the particular phytotoxicant(s) to which the plant has been exposed, and the like. In many embodiments, the amount of ACSE component in a composition may range from about 0.1% to about 20% w/w, e.g., from about 0.1% to about 18% w/w, e.g., from about 0.3% to about 16.0% w/w, e.g., from about 1.0% to about 10.0% w/w.

Water Component

The subject compositions may be aqueous or non-aqueous compositions, i.e., may be in solid form, semi-solid form or liquid form, where in certain embodiments the subject compositions are applied to a plant as a foliar spray. In embodiments that include an amount of liquid, the amount of liquid will vary such that the viscosity of a given composition may vary and range from low to high. For example, viscosities may range from about 1 centipoise ("cp") to about 50,000 cp, e.g., from about 10 cp to about 25,000 cp, e.g., from about 20 cp to about 15,000 cp. In those embodiments in which the compositions are aqueous compositions, they further include a suitable amount of water. The amount of water present in the composition may vary and may range from about 15% to about 99.9% w/w of water, e.g., about 25% to about 85% w/w of water, e.g., about 40% to about 70% w/w of water.

The water used in the subject composition may be obtained from any suitable source, e.g., a municipal water source and the like. In certain embodiments, purified water is employed, e.g., to dilute pesticide concentrates to provide application-ready pesticide formulations, to assist in mixing the composition components, etc. For example, water utilized to prepare application-ready pesticide compositions in accordance with this invention may be purified to have a total dissolved solids (TDS) content of about 1 to about 500 ppm in certain embodiments.

Additional Components

Embodiments of the subject compositions may also include one or more additional components such as, but not limited to, one or more macronutrient components and/or one or more micronutrient components and/or one or more vitamin/cofactor components and/or one or more complexing agents and/or one or more species of microbes. Other components such as buffers, surfactants, wetting agents, spreaders, emulsifiers, viscosity regulators, diluents, dispersing agents, foaming agents and foaming suppressants, penetrants, stickers, correctants and attractants, and the like may also be employed. For example, embodiments of the subject compositions may have a pH that ranges from about 1 to about 12, e.g., from about 3 to about 9, e.g., from about 5 to about 8. Accordingly, a suitable buffer may be employed to maintain a specific pH. Any suitable buffer may be used, e.g., phosphate, amino acid, polyhydroxy organic acid, and the like.

As noted above, a surfactant may be used. The term "surfactant" is used herein in its conventional sense to refer to a compound that effects reduction in the surface tension in a fluid. Surfactants may be used to increase the spreading and wetting properties of a pesticide composition. For example, surfactants may be used to increase spreading, coverage and penetration of a surface, e.g., hard and wet soils, to provide a more uniform distribution of a composition.

Examples of surfactants that may be employed in the subject compositions include anionic, cationic, amphoteric and nonionic surfactants. For example, nonionic surfactants that may be employed in certain embodiments include organosilicone surfactants. A particular organosilicone surfactant that may be used in certain embodiments is a surfactant that includes a combination of polyalkyleneoxide modified heptamethyltrisiloxane combined with allyloxypolyethyleneglycol methyl ether (e.g., available under the brand name SIL-WET L-77® surfactant available from GE Silicones of West Virginia). Other surfactants may also be used. Other, exemplary surfactants that may be employed include, but are not limited to, those provided in the table below.

| Generic Name | Exemplary Brand Name | Chemical Name | Category |
| --- | --- | --- | --- |
| organo-silicone spreader | Kinetic | Polyalkyleneoxide modified polydimethyl-siloxane and nonionic surfactants | wetter/spreader/penetrant |
| nonionic spreader | Active Plus | Alkylarylpolyoxy-ethylene glycols plus free fatty acids | nonionic spreader |
| nonionic spreader | Ad-Wet | Nonylphenoxypoly(ethyleneoxy) ethanol, isopropyl alcohol 2-methoxy ethanol, oleic acid 80% | spreader/penetrant |
| nonionic spreader | Amway All-Purpose Spray Adjuvant | alkyl aryl polyalkoxylated alcohols | wetting agent |
| nonionic spreader | Anchor | Cottonseed oil, alkylphenoxy polyethoxy ethanols | sticker/spreader |
| buffering agent | Balance | Alkyl aryl phosphoric acid ester, phosphoric acid | buffer/wetting agent |
| nonionic spreader | Bio-Film | Alkylarylpolyoxyethylene, fatty acids, glycol ethers, di-alkyl benzene, dicarboxylate, isopropanol | spreader/sticker |
| nonionic spreader | First Choice Spreader Sticker | Alkylarylpolyoxyethylene glycol, isopropyl alcohol | spreader/sticker |
| nonionic spreader | Frigate | Fatty amine ethyoxylate | adjuvant |
| anti-foam agent | No Foam Adjuvant | Nonyl phenoxy polyethoxy ethanol polydimethyl/siloxane | spreader/activator |
| nonionic spreader | Nu-Film-P | Poly-1-p-menthene | spreader/sticker |

Macronutrients

As noted above, the subject compositions may also include one or more macronutrient components for plant nutrition, development and growth. As the macronutrient components are components that are used by a plant, they are in a water soluble form that may be easily used by a plant. The subject compositions may include one or a plurality of macronutrient components. Accordingly, the number of macronutrient components present in a composition may range from about 1 to about 15 or more, e.g., from about 1 to about 6, e.g., from about 2 to about 6.

The total amount of macronutrient component present in a given composition (whether one or a plurality of macronutrients) depends on a variety of factors such as the particular plant to which the composition is to be administered, the particular macronutrient component(s) employed, the phytotoxicant, and the like. In many embodiments, the total amount of macronutrient component in the composition may range from about 0.0001% to about 0.5% w/w, e.g., from about 0.001% to about 0.3% w/w, e.g., from about 0.001% to about 0.2% w/w. Representative macronutrients are compounds that include one or more of (but which are not limited to): N, P, K, Ca, Mg, S, Cl, Na, C, H, and O. For example, certain embodiments may include one or more of the following exemplary macronutrient components:

N—ammonium nitrate, monoammonium phosphate, ammonium phosphate sulfate, ammonium sulfates, ammonium phosphatenitrate, diammonium phosphate, ammoniated single superphosphate, ammoniated triple superphosphate, nitric phosphates, ammonium chloride, aqua ammonia, ammonia-ammonium nitrate solutions, calcium ammonium nitrate, calcium nitrate, calcium cyanamide, sodium nitrate, urea, urea-formaldehyde, urea-ammonium nitrate solution (e.g., available under the brand name UAN-32 which is urea ammonium nitrate solution 32% (may also be known under other brand names such as URAN, SOLUTION 32 and 32% SOLUTION)), nitrate of soda potash, potassium nitrate, amino acids, proteins, nucleic acids, and the like. For example, ammonium polyphosphate, e.g., available under the brandname 10-34-0 available from Agrium of Canada may be employed.

P—superphosphate (single, double and/or triple), phosphoric acid; ammonium phosphate, ammonium phosphate sulfate, ammonium phosphate nitrate, diammonium phosphate, ammoniated single superphosphate, ammoniated single superphosphate, ammoniated triple superphosphate, nitric phosphates, potassium pyrophosphates, sodium pyrophosphate, nucleic acid phosphates, and the like;

K—potassium chloride, potassium sulfate, potassium gluconate, sulfate of potash magnesia, potassium carbonate, potassium acetate, potassium citrate, potassium hydroxide, potassium manganate, potassium phosphate, potassium molybdate, potassium thiosulfate, potassium zinc sulfate, and the like;

Ca—calcium ammonium nitrate, calcium nitrate, calcium cyanamide, calcium acetate, calcium acetylsalicylate, calcium borate, calcium borogluconate, calcium carbonate, calcium chloride, calcium citrate, calcium ferrous citrate, calcium glycerophosphate, calcium lactate, calcium oxide, calcium pantothenate, calcium proprionate, calcium saccharate, calcium sulfate, calcium tartrate, and the like;

Mg—magnesium oxide, dolomite, magnesium acetate, magnesium bensoate, magnesium bisulfate, magnesium borate, magnesium chloride, magnesium citrate, magnesium nitrate, magnesium phosphate, magnesium salicylate, magnesium sulfate, and the like;

S—ammonium sulfate, ammonium phosphate sulfate, calcium sulfate, potassium sulfate, magnesium sulfate, sulfuric acid, cobalt sulfate, copper sulfate, ferric sulfate, ferrous sulfate, sulfur, cysteine, methionine, and the like.

Micronutrients

As noted above, the subject compositions may also include one or more micronutrient components for plant nutrition and growth. As the micronutrient components are components that are used by a plant, they are in a water soluble form that may be easily used by a plant. The subject compositions may include one or a plurality of micronutrient components. Accordingly, the number of macronutrient components present in a composition may range from about 1 to about 60 or more, e.g., from about 3 to about 55, e.g., from about 4 to about 50.

The total amount of micronutrient component present in a given composition (whether one or a plurality of micronutrients) depends on a variety of factors such as the particular plant to which the composition is to be administered, the particular micronutrient component(s) employed, the phytotoxicant, and the like. In many embodiments, the total amount of micronutrient component in the composition may range from about 0.00000001% to about 0.1% w/w, e.g., from about 0.00000001% to about 0.5% w/w, e.g., from about 0.00000001% to about 0.005% w/w. Representative micronutrients are compounds that include one or more of (but which are not limited to): Zn, Fe, Mn, Cu, B, Mo, and Co. For example, certain embodiments may include one or more of the following exemplary micronutrient components:

Zn—zinc oxide, zinc acetate, zinc bensoate, zinc chloride, zinc citrate, zinc nitrate, zinc salicylate, ziram, and the like;

Fe—ferric chloride, ferric citrate, ferric fructose, ferric glycerophosphate, ferric nitrate, ferric oxide (saccharated), ferrous chloride, ferrous citrate ferrous fumarate, ferrous gluconate, ferrous succinate, and the like;

Mn—manganese acetate, manganese chloride, manganese nitrate, manganese phosphate, and the like;

Cu—cupric acetate, cupric butyrate, cupric chlorate, cupric chloride, cupric citrate, cupric gluconate, cupric glycinate, cupric nitrate, cupric salicylate, cuprous acetate, cuprous chloride, and the like;

B—calcium borate, potassium borohydride, borax, boron trioxide, potassium borotartrate, potassium tetraborate, sodium borate, sodium borohydride, sodium tetraborate, and the like;

Mo—molybdic acid, calcium molybdate, potassium molybdate, sodium molybdate, and the like;

Co—cobaltic acetate, cobaltous acetate, cobaltous chloride, cobaltous oxalate, cobaltous potassium sulfate, cobaltous sulfate, and the like.

Vitamins and Cofactors

As noted above, the subject compositions may also include one or more vitamin/cofactor components. As the vitamin/cofactor components are components that are used by a plant, they are in a water soluble form that may be easily used by a plant. The subject composition may include one or a plurality of vitamin/cofactor components. Accordingly, the number of vitamin/cofactor components present in a composition may range from about 1 to about 20 or more, e.g., from about 3 to about 15, e.g., from about 5 to about 12.

The total amount of vitamin/cofactor component present in a given composition (whether one or a plurality of vitamin/cofactor components) depends on a variety of factors such as the particular plant to which the composition is to be administered, the particular vitamin/cofactor component(s) employed, the phytotoxicant, and the like. In many embodiments, the total amount of vitamin/cofactor component in the composition may range from about 0.00000001% to about 0.1% w/w, e.g., from about 0.0000001% to about 0.05% w/w, e.g., from about 0.000001% to about 0.01% w/w. Exemplary vitamin/cofactor components include, but are not limited to:

Thiamine—thiamine pyrophosphate, thiamine monophosphate, thiamine disulfide, thiamine mononitrate, thiamine phosphoric acid ester chloride, thiamine phosphoric acid ester phosphate salt, thiamine 1,5 salt, thiamine triphosphoric acid ester, thiamine triphosphoric acid salt, yeast, yeast extract, and the like;

Riboflavin—riboflavin acetyl phosphate, flavin adenine dinucleotide, flavin adenine mononucleotide, riboflavin phosphate, yeast, yeast extract, and the like;

Nicotinic acid—nicotinic acid adenine dinucleotide, nicotinic acid amide, nicotinic acid benzyl ester, nicotinic acid monoethanolamine salt, yeast, yeast extract, nicotinic acid hydrazide, nicotinic acid hydroxamate, nicotinic acid-N-(hydroxymethyl)amide, nicotinic acid methyl ester, nicotinic acid mononucleotide, nicotinic acid nitrile, and the like;

Pyridoxine—pyridoxal phosphate, yeast, yeast extract, and the like;

Folic acid—yeast, yeast extract, folinic acid, and the like;

Biotin—biotin sulfoxide, yeast, yeast extract, biotin 4-amidobenzoic acid, biotin amidocaproate N-hydroxysuccinimide ester, biotin 6-amidoquinoline, biotin hydrazide, biotin methyl ester, d-biotin-N-hydroxysuccinimide ester, biotin-maleimide, d-biotin p-nitrophenyl ester, biotin propranolal, 5-(N-biotinyl)-3 aminoallyl)-uridine 5'-triphosphate, biotinylated uridine 5'-triphosphate, N-e-biotinyl-lysine, and the like;

Pantothenic acid—yeast, yeast extract, coenzyme A, and the like;

Cyanocobalamin—yeast, yeast extract, and the like;

Phosphatidylcholine—soybean oil, eggs, bovine heart, bovine brain, bovine liver, L-a-phosphatidylcholine, B-acetyl-g-O-alkyl, D-a-phosphatidylcholine(PTCn), B-acetyl-g-O-hexadecyl, DL-a-PTCh,B-acetyl-g-O-hexadecyl, L-a-PTCh, B-acetyl-g-O-(octadec-9-cis-e-nyl), L-a-PTCh, B-arachidonoyl, g-stearoyl, L-a-PTCh, diarachidoyl, L-a-PTCh, dibehenoyl(dibutyroyl, dicaproyl, dicapryloyl, didecanoyl, dielaidoyl, 12 diheptadecanoyl, diheptanoyl), DL-a-PTCh dilauroyl, La-PTCh dimyristoyl(dilauroyl, dilinoleoyl, dinonanoyl, dioleoyl, dipentadeconoyl, dipalmitoyl, distearoyl, diundecanoyl, divaleroyl,B-elaidoyl-a-palmitoyl, B-linoleoyl-a-palmitoyl)DL-a-PTCh di-O-hexadecyl(dioleoyl, dipalmitoyl, B-O-methyl-g-O-hexadecyl, B-oleoyl-g-O-hexadecyl, B-palmitoyl-g-O-hexadecyl), D-a-PTCh dipalmitoyl, L-a-PTCh, B-O-methyl-g-O-octadecyl, L-a-PTCh, B-(NBD-aminohexanoyl)-g-pal-mitoyl, L-a-PTCh, B-oleoyl-g-O-palmitoyl(stearoyl), L-a-PTCh, B-palmitoyl-g-oleoyl, L-a-PTCh, B-palmitoyl-a-(pyren 1-yl)hexanoyl, L-a-PTCh, B(pyren-1-yl)-decanoyl-g-palmitoyl, L-a-PTCh, B-(pyren-1-yl)-hexanoyl-g-palmitoyl, L-a-PTCh, B-stearoyl-g-oleoyl, and the like;

Inositol—inositol monophosphate, inositol macinate, myo-inositol, epi-inositol, myo-inositol 2,2'anhydro-2-c-hydroxymethyl(2-c-methylene-my-oinositol oxide), D-myo-inositol 1,4-bisphosphate, DL-myo-inositol 1,2-cyclic monophosphate, myo-inositol dehydrogenase, myo-inositol hexanicotinate, inositol hexaphosphate, myo-inositol hexasulfate, myo-inositol 2-monophosphate, D-myo-inositol 1-monophosphate, DL-myo-inositol 1-monophosphate, D-Myo-inositol triphosphate, scyllo-inositol, and the like;

PABA—m-aminobenzoic acid, O-aminobenzoic acid, p-aminobenzoic acid butyl ester, PABA ethyl ester, 3-ABA ethyl ester, and the like.

Complexing Agents

As noted above, the subject compositions may also include one or more complexing agents. A complexing agent is an agent that aids in the solubilization of other components in the composition which otherwise may precipitate and become non-assimilable or difficultly assimilable. For example, a complexing agent such as citric acid, humic acids, lignosulfonate, etc. may serve to tie up ions such as iron and other ions and prevent them from forming precipitates such that a complexing agent may be an agent that is capable of complexing with a metal ion. In some cases, e.g., with EDTA, this complexing is by way of a process of chelation. The component, e.g., macronutrient or micronutrient, so complexed nevertheless remains assimilable. As such, complexing agents may be described as agents which act to facilitate transfer of other components into the cell structure of a plants. As the complexing agents are used by a plant, they are typically water soluble agents.

The subject composition may include one or a plurality of complexing agents. Accordingly, the number of complexing agents present in a composition may range from about 1 to about 35 or more, e.g., from about 1 to about 20, e.g., from about 1 to about 10.

The total amount of complexing agent present in a given composition (whether one or a plurality of complexing agents) depends on a variety of factors such as the particular plant to which the composition is to be administered, the particular complexing agent(s) employed, and the like. In many embodiments, the total amount of complexing agent in the composition may range from about 0.01% to about 30% w/w, e.g., from about 0.1% to about 25% w/w, e.g., from about 1.0% to about 20% w/w. Exemplary complexing agent components include, but are not limited to: citric acid, lignosulfonates, e.g., Ca—, K—, Na—, and ammonium lignosulfonates, fulvic acid, ulmic acid, humic acid, amino acids, nucleic acids, ethylenediamin tetraacetatic acid (EDTA), diethylene triamine pentacetic acid (DTPA), nitrolotriacetic acid (NTA), ethylenediaminediacetate (EDDA), ethylenedi-aminedi(o-hydroxyphenylacetic) acid (EDDHA), hydroxy-ethylethylene-diaminetriacetic acid (HEDTA), cyclohexane diamine tetraacetic acid (CDTA), and the like.

Naturally occurring chelating agents may also be employed. By naturally occurring chelating agent is meant that the chelating agent is a chelating agent that occurs in nature, i.e. not an agent that has been first synthesized by human intervention. The naturally occurring chelating agent may be a low molecular weight chelating agent, where by low molecular weight chelating agent is meant that the molecular weight of the chelating agent does not exceed about 200 daltons. In many embodiments, the molecular weight of the chelating agent is greater than about 100 daltons.

Naturally occurring low molecular weight chelating agents that may be used are microbial produced chelating agents. By "microbial produced" is meant that the chelating agent is produced by a microbe, where the microbe is generally a bacterium or a fungus. In many embodiments, the chelating agents are citric acid cycle intermediates and derivatives thereof. Specific chelating agents of interest include: malic acid, succinic acid, oxalacetic acid, ketoglutaric acid and citric acid and amino acids derived from citric acid cycle intermediates, such as glycine (75.1 daltons), alanine (89.1 daltons), serine (105.1 daltons), valine (117.2 daltons), threonine (119.1 daltons), cysteine (121.2 daltons), leucine (131.2 daltons), isoleucine (131.2 daltons), asparginine (132.1 daltons), glutamine (146.2 daltons), methionine (149.2 daltons), etc.

Accordingly, embodiments include compositions that may include a source of at least one naturally occurring chelating agent. By source is meant that the compositions may include the chelating agents or an entity or component that produces the chelating agents. In many embodiments, the source of chelating agents is a living or viable microbial source of chelating agents. For example, the microbial source may be a bacterial or fungal culture which produces the requisite chelating agents.

Microbes

As noted above, the subject compositions may include one or a plurality of distinct microbial species. By plurality is meant at least about 2, e.g., about 3, e.g., about 5, where in certain embodiments the number of different microbial species in a subject compositions may be as high as about 10 to about 15 or higher. A microbial species present in a subject composition may serve a variety of functions, e.g., may be antagonistic against one or more microbial pathogens. By antagonistic against one or more microbial pathogens is meant that microbial species inhibits the growth of one or more pathogenic microbial species, e.g., as determined by a y suitable methods, e.g., a suitable assay or the like.

The one or more microbial species provided in a subject composition may be any suitable microbial species, including bacterial species and fungal species, where the specific microbial specie(s) employed in a given composition may depend on a variety of factors, e.g., the particular plant, soil, phytotoxicant, etc. Exemplary bacterial species of interest include, but are not limited to: *Bacillus subtilis; Bacillus thuringiensis; Bacillus cereus; Bacillus megaterium; Bacillus penetrans; Arthrobacter paraffineus;* and *Pseudomonas fluorescens*. Exemplary fungal species of interest include, but are not limited to: *Trichoderma viride, Trichoderma harzianum, Trichoderma polysporum, Trichoderma hamatum, Trichoderma koningii, Gliocladium virens, Gieocladium roseum, Gliocladium catenulatum, Penicillium oxalicum, Penicillium lilacinum, Penicillium nigricans, Penicillium chrysogenum, Penicillium frequenters*, and the like.

A plurality of microbial species may be employed in the practice of the subject methods and include spore-forming and non-spore forming bacterial species and beneficial fungal species, such as available under the trademark IOTA. IOTA is a trademark of Fusion 360 of Turlock, Calif. for a microbial inoculant for soil and generally includes spore-forming and non-spore forming bacterial species and beneficial fungal species (see also, U.S. patent application Ser. No. 09/695,531 entitled "MICROBIAL BLEND COMPOSITIONS AND METHODS FOR THEIR USE", the disclosure of which is herein incorporated by reference).

The subject compositions may include a substrate for activating the proliferation of certain microbes, e.g., may include TILTH or an analogous substance. TILTH is a trademark of Fusion 360 of Turlock, Calif. for a specifically formulated substrate designed to activate rapid proliferation of most beneficial microbial saprophytes, symbionts and/or competitors of plant pathogens. In general TILTH includes complex carbohydrates, variable chain alcohols, catalysts, polycarboxylic acids, amino acids and complex proteins.

Exemplary Compositions

As described above, embodiments of the subject compositions at least include an assimilable carbon skeleton energy component. However, certain embodiments include one or more additional components as described above. Plant formulations that include one or more components as described above and which may be employed in the subject invention include, but are not limited to, those described in, and analogous to those described in, U.S. Pat. Nos. 5,797,976; 5,549, 729 and 6,309,440, the disclosures of which are herein incorporated by reference. A particularly effective composition that may be used in the practice of the subject methods may include an ACSE component, e.g., GREEN THUMB™ 1-0-2 plant constituent formulation, or an analogous formulation. GREEN THUMB 1-0-2 is a trademark of Fusion 360 of Turlock, Calif. for a plant constituent formulation. In general, GREEN THUMB 1-0-2 plant constituent formulation includes a carbon skeleton energy component, nitrogen (urea nitrogen and nitrate nitrogen), potassium ($K_2O$), calcium, magnesium, zinc, manganese and iron. Also of interest is the combination of an ACSE component, e.g., GREEN THUMB 1-0-2, with a source of soluble calcium and nitrogen, e.g., as provided by INTEGRITY (also referred to as INTEGRITY CALCIUM) which is a trademark of Fusion 360 of Turlock, Calif. for a soluble, calcium mineral plant supplement. INTEGRITY includes nitrogen (2% ammoniacal nitrogen and 2% nitrate nitrogen) and calcium (Ca) derived from calcium acetate, calcium gluconate, calcium chloride and calcium nitrate. Such compositions may also include a surfactant such as an organosilicone surfactant (e.g., SILWET L-77).

For example, an exemplary composition that may be used in the practice of the subject methods may include an ACSE component, e.g., GREEN THUMB 1-0-2 or analogous substance (e.g., about 2 to about 5 gallons/100 gallons composition), a calcium component, e.g., INTEGRITY CALCIUM or analogous substance (e.g., about 2 to about 4 quart/100 gallons composition) and a surfactant such as an organosilicone surfactant, e.g., SILWET L-77 (e.g., about 2 to about 3 ounces/100 gallons composition). Such embodiments are particularly useful as a remedial spray.

Other composition embodiments may include urea ammonium nitrate, ammonium polyphosphate, a plurality of microbial species and a substrate for the proliferation of microbes. An exemplary embodiment of a composition that may employ these components and which may be used in the practice of the subject methods may include UAN-32 or analogous substance (e.g., about 5 to about 25 gallons/acre), 10-34-0 or analogous substance (e.g., about 1 to about 5 gallon/acre), water e.g., about 4 to about 10 gallons/acre), TILTH or analogous substance (e.g., about 40 to about 100 gallons/acre), and ITOA or analogous substance (e.g., about 1 to about 5 gallon/acre). Such embodiments are particularly useful for soil bioremediation.

Composition Preparation

In general, the compositions used in the practice of the subject methods are prepared by combining one or more of the components described above (e.g., one or more of: an assimilable carbon skeleton energy component and/or water and/or a macronutrient component and/or a micronutrient component and/or a complexing agent and/or a vitamin/cofactor and/or one or more microbial species), each in amounts sufficient to yield the a composition effective at treating a plant identified as one which has been exposed to, or is at least suspected of being exposed to, a phytotoxicant.

The various components used to produce the subject pesticide compositions may be obtained from any convenient source and/or produced using conventional protocols known to those of skill in the art. For example, the water that is used to produce the subject compositions may be tap water obtained from any convenient water source, e.g. a municipal water district, where the water may be purified or otherwise treated, e.g. to remove certain undesirable agents that may be initially present therein. The various other components may be obtained from any convenient source, e.g. commercial vendors.

In certain embodiments, a composition may be prepared in a mix tank (e.g., a spray tank or analogous mixing apparatus). For example, such embodiments may include tank mixing in a spray tank by combining an assimilable carbon skeleton energy component and/or water and/or a macronutrient component and/or a micronutrient component and/or a vitamin/ cofactor component and/or a complexing agent and/or one or more microbial species in such a mixing apparatus or other analogous apparatus. In certain embodiments a tank mix may be prepared by combining one or more commercially obtained components, e.g., obtained in dry form, and in a spray tank with water. Some or all of the components of a composition used in the practice of the subject invention may be pre-formulated, i.e., provided to the end user in a pre-mixed, ready-to use form. In instances wherein a parent mix or concentrate is use as a starting material, the subject methods may also include a dilution step, in which water is combined with the concentrate in order to reduce the concentration of the components in the composition.

As noted above, one or more other components may also be included in the subject compositions (e.g., one or more buffers, surfactants, wetting agents, spreaders, emulsifiers, viscosity regulators, diluents, dispersing agents, foaming agents and foaming suppressants, penetrants, stickers, correctants, attractants, and the like). Accordingly, any other component may be added to a given composition and mixed therewith, e.g., in a tank mixer. For example, in those embodiments where a surfactant is used, such may be added to a tank after all other components are added in order to minimize foam generation. Embodiments may also include an anti-foam agent, e.g., Foambuster, and the like. Foambuster is the brand name of a dimethylpolysiloxane-containing anti-foaming agent available from Helena Development Lab and is designed to minimize or prevent foaming problems associated with some pesticides in water-based sprays. In such instances, an anti-foaming agent may be added to a tank prior to the addition of a surfactant.

Components of a given composition may be packaged separately or together at a manufacturing site and transported to a user for use. For example, a manufacturer, distributor, retail outlet, etc., may package specific components separately, with specific instructions for combining the components in suitable ratios to produce a composition for use that at least reduces pesticide phytotoxicity and/or instructions for applying the composition to a plant to combat phytotoxicity. In such instances, .a user may then receive the separately packaged components and instructions and combine the components together according to the instructions to provide a composition that may be used in the practice of the subject methods. Embodiments may also include packaged compositions wherein some or all of the component are mixed together (i.e., pre-formulated), e.g., at a manufacturing site, distributor, etc., such that some or all of the components are combined prior to packaging of the components. Such embodiments may include instructions for mixing one or more other components and/or for further processing and/or instructions for applying a composition to a plant to treat the plant for phytotoxicity.

Application of a Composition to a Plant

Once a plant has been identified as being exposed to a phytotoxicant and a composition for application to the plant has been prepared (if not provided pre-formulated), a suitable amount of a phytotoxicity-fighting composition may be applied to a plant using any suitable method. A composition may be applied to the plant and/or to soil associated with the plant. Accordingly, in practicing the subject methods, a composition as described above is applied to at least a portion of the plant, e.g., at least a portion of the foliage of the plant. By "application" is meant that the composition is placed on the surface of the plant and/or in or on the soil associated with the plant, including in the water used to irrigate the plant. For example, a composition may be placed on the surface of the foliage of the plant(s) to be treated, where the term "foliage" is used broadly to encompass not only the leaves of the plant, but every other part of the plant that is not underground, i.e. below the soil surface, such that the term "foliage" includes leaves, stems, flowers, fruit, etc. In certain embodiments, a composition may be contacted with the soil and in this context contact is meant that the composition is introduced to the soil, e.g., contact may include spraying so that the composition soaks into the soil, injecting the composition into the soil, flooding the soil with the composition, and the like. Accordingly, application to a plant may be by any convenient method, including spraying (e.g., spraying onto foliage and spraying onto soil surfaces), injection into irrigation water such as through sprinkler systems, including into drip or micro sprinkler systems, injection into flood or furrow runs, delivered through shanking, etc.

The amount of a given composition used during any one application will vary greatly depending on the nature of the plant and the number of plants to be treated (e.g., acreage), the nature of the composition, the environmental conditions, the particular phytotoxicant, the degree of phytotoxicity, etc. Where more than one plant is treated, e.g., where crops are treated, the amount that is applied based on acreage may range from about 10 gal per acre to about 250 gallons per acre, e.g., from about 15 to about 225 gal per acre, e.g., from about 20 to about 200 gal per acre.

Depending on the nature of the plant, the phytotoxicant, the degree of phytotoxicity, the nature of the composition, the environmental conditions, as well as other factors, the composition may be applied more than once over a given period of time. As such, a composition may be applied daily, weekly or a few times/week, every two weeks, monthly etc. For example, applications may include a first, remedial spray application followed by one or more subsequent applications, e.g., at least about 2-3 additional spray applications, at intervals of about every 2 to about every 20 days—and thereafter until appropriate to stop, e.g., phytotoxicity is stopped or otherwise managed and/or the plant and/or soil is determined to be healthy (e.g., as determined by return to normal plant growth/development relative to the growth/development of the plant suffering from phytotoxicity—i.e., growth/development of the plant prior to experiencing phytotoxicity). For example, remediation of a phytotoxicant may be observed by plant coloration, leaf size, bioassays of plant and/or soil, and the like. In certain embodiments applications of a composition to a plant may be repeated, e.g., repeated regularly on a schedule that may range from about every 2 to about every 20 days as needed or even throughout the plant's entire growing season.

In instances where a composition is applied more than once over a given period of time, subsequent applications may differ in one or more respects, e.g., compositions may change (i.e., different compositions may be employed, different ratios of a composition's components, etc.), methods of application may differ, etc.

Embodiments may also include soil remediation, e.g., soil bioremediation, and remedial spraying, e.g., in instances where soil is contaminated with a phytotoxicant. Such embodiments may include, at some point after planting in phytotoxicant-contaminated soil, applying a composition to the soil and to the foliage of the plant. For example, at some point after planting in contaminated soil (e.g., from about 1 day to about 6 months after planting), a composition may be applied to the soil by injection of the composition into the sprinkler system for an even distribution of the soil. In certain embodiments, suitable solid remediation will be accomplished in about 1 to about 10 applications, e.g., from about 1 to about 5 applications, where the number of application will depend on a variety of factors such as, but not limited to, the toxicant species, the extent of the contamination and/or toxicity, the intensity of the remedial program, and the like. For example, in the instances where the toxic factor includes pathogens and/or pests, in certain embodiments an initial, intense activation may be followed by one or more periodic, regular maintenance applications. In addition to the soil remediation, a composition in the form of a foliar spray may be applied to the foliage of the plant(s) planted in the soil in a manner analogous to that described above, e.g., spray applications may include a first spray application followed by subsequent applications that may include at least about 2 to about 3 additional spray application—sprayed on the plant in intervals that may range from about every 2 to about every 20 days.

The subject methods, i.e., application of a composition to a plant exposed to a phytotoxicant, results at least in the reduction of phytotoxicity in a plant and/or recovery of normal physiological functions. In certain embodiments complete elimination of phytotoxicity may be achieved by the practice of the subject methods. Furthermore, in certain embodiments the subject methods may be employed to impart preventive tolerance to the treated plant to phytotoxicity. Accordingly, the practice of the subject invention may be used to mollify the phytotoxicity of a plant and/or completely detoxify a plant of a phytotoxicant. The subject methods may result in inciting enhanced production of membrane tissues and concomitant production of enzymes needed for efficient physiological functions and/or de novo synthesis of toxicant degradative enzymes.

Utility

The subject methods find use in a variety of applications where a plant is suffering from, or is suspected of suffering from, phytotoxicity due to exposure to a phytotoxicant. Accordingly, the subject methods may be used on any number of different types of plants, e.g., any plant for which a pesticide is registered for use with the Environmental Protection Agency's (EPA's) Office of Pesticide and/or an appropriate state agency.

Exemplary types of plants that may be treated using the subject methods include, but are not limited to, cereal crops (e.g., Rice, Wheat, Corn, Barley, Oats, Sorghum, Rye, Millet, and the like); legumes (e.g., Soybean, Peanut, Beans, Broad Bean, Pea, Chickpea or Garbanzo, Black Eyed Pea, Lentil, Pigeon Pea, Guar, and the like); forage crops (e.g., Clover, Bird's Foot Trefoil, Vetch, Sweet Clover, Lespedeza, Lupine, Sorghum-Sudan, Kentucky Bluegrass, Timothy, Orchardgrass, Fescua, Bermudagrass, Dallisgrass & Bahiagrass, Ryegrass, Bentgrass and the like); stem and leaf crops (e.g., Sugar Cane, Artichoke, Asparagus, Broccoli, Brussels Sprouts, Cabbage, Celery, Chard, Chinese Cabbage, Collards, Endive, Lettuce, Parsley, Rhubarb, Spinach and the like); root crops (e.g., Potato, Cassave, Sweet Potato, Beets, Taro, Carrot, Horseradish, Jerusalem artichoke, Onion, Parsnip, Radish, Rutabaga, Salsify, Turnip, Yam, and the like); fruit and seed vegetables (e.g., Tomato, Eggplant, Curcurbits, Okra, Pepper, and the like); fruit and nut crops (e.g., Citrus, Grape, Banana, Apple, Stone Fruits, Blueberry, Brambles, Cranberry, Currant, Pear, Avocado, Cashew, Coconut, Date, Fig, Guava, Litchi, Maracuja, Mango, Olive, Papaya, Pineapple, Pomegranate, Almond, Brazil Nut, Filberts, Macadamia, Pecan, Pistachio, Walnuts, Sunflower and the like); beverage crops (e.g., Coffee, Tea, Cacao, Cola, Hops, and the like); oil, fat and wax crops (e.g., Safflower, Coconut, African Oilpalm, Castor Bean, Rape, Sesame, Sunflower, Linseed, Tung, Soybean, Carnauba, Candelilla, Jojoba, and the like); spices, perfumes an flavorings (e.g., Black Pepper, Cinnamon, Clove, Vanilla, Mint, Oregana, Allspice, Anise, Angelica Oil, Mustard, Sage, Ginger, Rose Oil, Bergamot, Camphor, Cananga, Citronella Grass, Eucalyptus, Geranium Oil, Lavandula, Rosemary, Thyme, Turpentine, and the like); ornamentals, forest and fiber crops (e.g., Cotton, Flax, Hemp, Christmas Trees (various conifers), Ornamental Evergreens, Rose, Chrysanthemum, Carnation, Iris, Azalea, Rhododendron, and the like); and houseplants (various species).

The subject methods find use in at least reducing phytotoxicity. By at least reducing pesticide phytotoxicity is meant that at least one aspect or indicator of phytotoxicity is at least reduced relative to phytotoxicity observed prior to the practice of the subject methods. In certain embodiments, phytotoxicity may be completely eliminated such that substantially no, including no, effects of phytotoxicity may be observed.

Systems

Also provided by the subject invention are systems. The subject systems may include one or more of the following: a carbon-skeleton energy component and/or a macronutrient component and/or a micronutrient component and/or a vitamin/cofactor component and/or a complexing agent and/ore microbial component (e.g., microbial blend composition). Water may also be provided in a subject system. In certain embodiments, a system of the subject invention may include one or more of the above-described components mixed together, e.g., one or more of the above mixed together with water, which mixture may be in a form suitable for application to a plant suffering from phytotoxicity (e.g., for spraying (e.g., spraying onto foliage and spraying onto soil surfaces), injection into irrigation water such as through sprinkler systems, including into drip or micro sprinkler systems, injection into flood or furrow runs, delivered through shanking, etc.).

Other components that may be provided in a subject system include but are not limited to one or more of: buffers, surfactants, wetting agents, spreaders, emulsifiers, viscosity regulators, diluents, dispersing agents, foaming agents and foaming suppressants, penetrants, stickers, correctants and attractants, and the like.

In certain embodiments, subject systems may include one or more of: GREEN THUMB™ 1-0-2 plant constituent formulation, or an analogous formulation, INTEGRITY or other analogous soluble, calcium mineral plant supplement, a surfactant, e.g., SILWET 77 or analogous surfactant, and BUD-SET or other analogous composition.

Suitable apparatus for mixing a composition to be employed in the subject methods and/or for applying a composition to a plant in need thereof in accordance with the subject methods may also be included in a subject system and include, but are not limited to: e.g., mixing tank, spray tank or other foliar spray apparatus, sprinkler system, etc. Accordingly, systems may include an apparatus for applying a composition to a plant using sub-surface methods, surface methods, aerial spraying, etc., where such may include an apparatus for aerial spraying, a tractor, a spray rig, a blaster, a device for hand spraying, etc.

Systems of the subject invention may also include instructions for use for practicing the subject methods, i.e., for applying a phytotoxicant-fighting composition of the subject invention to a plant in a manner to at least reduce phytotoxicity. The instructions may be printed on a suitable recording medium. For example, the instructions may be printed on a substrate, such as paper or plastic, etc. or may be present as an electronic, magnetic or optical storage data file present on a suitable computer readable storage medium, e.g., CD-ROM, diskette, etc. In yet other embodiments, the system may include means for obtaining the instructions from a remote source, e.g., via the Internet, may be provided. An example of this embodiment is a system that includes a World Wide Web address where the instructions may be viewed and/or from which the instructions may be. downloaded. Some form of access security or identification protocol may be used to limit access to those entitled to use the subject invention.

Kits

Also provided by the subject invention are kits. The subject kits may include one or more, including all, components that may be used to prepare a composition for use in practicing the subject methods. For example, kits may include a carbon-skeleton energy component and/or a macronutrient component and/or a micronutrient component and/or a vitamin/ cofactor component and/or a complexing agent and/ore microbial component (e.g., microbial blend composition). One or more, including all, of the components may already be combined together or pre-formulated: In those embodiments where more than two components are provided in a kit, the components may already be combined together and as such may be packaged in a single container such as a vial, bottle, can, pouch, bag, canister, and the like. In other embodiments, two or more components of a kit may be packaged separately, i.e., not pre-formulated. As such, embodiments may include kits that include one or more separate containers such as vials, can, bottles, pouches, bags, canisters, and the like, each container containing a separate component to be used to make a composition for use in the subject methods.

Kits may also include one or more other components for use in preparing a composition in accordance with the subject invention. Accordingly, kits may include one or more of: buffers, surfactants, wetting agents, spreaders, emulsifiers, viscosity regulators, diluents, dispersing agents, foaming agents and foaming suppressants, penetrants, stickers, correctants and attractants, and the like. These components, if provided in a kit, may be provided pre-formulated with one or more other components of the kit, or may be provided in a separate container, e.g., vial, bottle, can, pouch, bag, canister, and the like.

Kits may also include instructions for preparing a phytotoxicant-fighting composition, e.g., for combining one or more components to provide a composition, and/or instructions for applying a prepared composition to a plant to at least reduced phytotoxicity. The instructions may be printed on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic, magnetic or optical storage data file present on a suitable computer readable storage medium, e.g., CD-ROM, diskette, etc. In yet other embodiments, the instructions may not themselves be present in the kit, but means for obtaining the instructions from a remote source, e.g., via the Internet, may be provided. An example of this embodiment is a kit that includes a World Wide Web address where the instructions may be viewed and/or from which the instructions may be downloaded. Some form of access security or identification protocol may be used to limit access to those entitled to use the subject invention.

EXPERIMENTAL

The following examples are put forth so as to provide those of ordinary skill in the art with a complete disclosure and description of how to make and use the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

In the following set of experiments, various plants were identified as exposed to various phytotoxicants. The identified plants were treated for phytotoxic effects of the respective phytotoxicants by application of various phytotoxicant-fighting compositions. In certain instances contaminated soil was also treated.

A. Herbicide (and Other Chemicals) Drift Phytotoxicity

1. Drift from the Herbicide Glyphosate (ROUNDUP)

In this set of experiments, almond trees, peach trees and grapevines experiencing phytotoxicity from drift of the phytotoxicant glyphosate (ROUNDUP) were treated according to the subject invention.

a. Drift onto Almonds Trees
Protocol

The protocol was initiated seven days after drift contamination. Prior to commencement of the treatment protocol, observations included new growth manifesting spindly leaf shape and chlorotic foliage typical of phytoxocity.
Remedial Spray:

| Material | Rate/100 gallons |
| --- | --- |
| GREEN THUMB 1-0-2 | 5 gallons |
| INTEGRITY CALCIUM | 4 quarts |
| SILWET L-77 | 3 ounces |

To prepare the composition for use, a spray tank was filled at least ³/₄ full with water and agitated before blending the above-described materials. The materials were added to the spray tank and blended together.

The composition was applied to the trees at a volume that delivers a fine mist (about 25-about 80 gallons per acre). Application of the composition to the trees was repeated which included at least 3 consecutive sprays at 5 day intervals and thereafter every 7-10 days until the trees recovered from the phytotoxicity.

Results restoration of normal growth by the second spray;

no limb or tree mortality;

new growth volume and quality was substantial with larger, thicker leaves, relative to that observed prior to performing the above-described protocol (superior growth above that normally observed in non-phytotoxic plants); and no carryover of the phytotoxicant ROUNDUP into successive seasonal growth.

Conclusions

The phytotoxicant-exposed trees were successfully treated for phytotoxicity according to the subject methods.

b. Drift onto Peach Trees
Protocol

The protocol was initiated twelve days after drift contamination. Prior to commencement of the treatment protocol, observations included chlorotic older and new leaves, new chlorotic foliage that was manifesting typical spindle shape, limbs that were exuding gum from buds and advanced stages of toxicity with onset of defoliation.
Remedial Spray:

| Material | Rate/100 gallons |
| --- | --- |
| GREEN THUMB 1-0-2 | 5 gallons |
| INTEGRITY CALCIUM | 4 quarts |
| SILWET L-77 | 3 ounces |

To prepare the composition for use, a spray tank was filled at least ¾ full with water and agitated before blending the above-described materials. The materials were added to the spray tank and blended together.

The composition was applied to the trees at a volume that delivers a fine mist (about 25-about 80 gallons per acre). Application of the composition to the trees was repeated which included at least 3 consecutive sprays at 5 day intervals and thereafter every 7-10 days until the trees recovered from the phytotoxicity.

Results restoration of normal growth by the fourth spray;

no tree mortality;

no carryover of the phytotoxicant ROUNDUP into successive seasonal growth.

Conclusions

The phytotoxicant-exposed trees were successfully treated for phytotoxicity according to the subject methods.

c. Drift onto Grapevines
Protocol

The protocol was initiated six days after drift contamination. Prior to commencement of the treatment protocol, observations included new foliage with compressed growth and palm-like veination and mature foliage that had incipient chlorosis.
Remedial Spray:

| Material | Rate/100 gallons |
| --- | --- |
| GREEN THUMB 1-0-2 | 5 gallons |
| INTEGRITY CALCIUM | 4 quarts |
| SILWET L-77 | 3 ounces |
| BUD-SET | 12 ounces |

To prepare the composition for use, a spray tank was filled at least ¾ full with water and agitated before blending the above-described materials. The materials were added to the spray tank and blended together.

The composition was applied to the vines at a volume that delivers a fine mist (about 25-about 80 gallons per acre). Application of the composition to the vines was repeated which included at least 3 consecutive sprays at 5 day intervals and thereafter every 7-10 days until the vines recovered from the phytotoxicity.

Results restoration of normal growth by the third spray;

no vine mortality;

treated vines manifesting thicker, larger leaves;

no carryover of the phytotoxicant ROUNDUP into successive seasonal growth.

Conclusions

The phytotoxicant-exposed vines were successfully treated for phytotoxicity according to the subject methods.

2. Drift from the Triazine Herbicide Simazine onto Strawberry Vines

In this experiment, strawberry vines experiencing phytotoxicity from drift of the phytotoxicant simazine were treated according to the subject invention.

protocol

The protocol was initiated eight days after drift contamination. Prior to commencement of the treatment protocol, observations included new and older growth manifesting chlorosis and new growth that was stunted and misshapen.
Remedial Spray:

| Material | Rate/100 gallons |
| --- | --- |
| GREEN THUMB 1-0-2 | 5 gallons |
| INTEGRITY CALCIUM | 4 quarts |
| SILWET L-77 | 3 ounces |
| BUD-SET | 12 ounces |

To prepare the composition for use, a spray tank was filled at least ¾ full with water and agitated before blending the above-described materials. The materials were added to the spray tank and blended together.

The composition was applied to the vines at a volume that delivers a fine mist (about 25-about 80 gallons per acre). Application of the composition to the vines was repeated which included at least 3 consecutive sprays at 5 day intervals and thereafter every 7-10 days until the vines recovered from the phytotoxicity.

Results
restoration of normal growth by the third spray;
no vine mortality;
treated vines manifested thicker stems, larger flowers and thicker leaves.

Conclusions

The phytotoxicant-exposed vines were successfully treated for phytotoxicity according to the subject methods.

3. Drift from the Dormancy-Breaking Substance DORMEX onto Lemon Trees

In this experiment, lemon trees experiencing phytotoxicity from drift of the phytotoxicant DORMEX were treated according to the subject invention.

Protocol

The protocol was initiated twelve days after drift contamination. Prior to commencement of the treatment protocol, observations included foliage with typical interveinal chlorosis and general tree appearance of stunted growth and off-color.

Remedial Spray:

| Material | Rate/100 gallons |
| --- | --- |
| GREEN THUMB 1-0-2 | 2 gallons |
| INTEGRITY CALCIUM | 2 quarts |
| SILWET L-77 | 2 ounces |

To prepare the composition for use, a spray tank was filled at least ¾ full with water and agitated before blending the above-described materials. The materials were added to the spray tank and blended together.

The composition was applied to the trees at a volume that delivers a fine mist (about 100-about 200 gallons per acre). Application of the composition to the trees was repeated which included at least 3 consecutive sprays at 5 day intervals and thereafter every 7-10 days until the trees recovered from the phytotoxicity.

Results
restoration of normal growth by the third spray;
no limb or tree mortality;
no carryover of DORMEX into successive seasonal growth.

Conclusions

The phytotoxicant-exposed trees were successfully treated for phytotoxicity according to the subject methods.

4. Drift from the Phenoxy Herbicide 2,4-D onto Grapevines

In this experiment, grapevines experiencing phytotoxicity from drift of the phytotoxicant 2,4-D were treated according to the subject invention.

Protocol

The protocol was initiated six days after drift contamination. Prior to commencement of the treatment protocol, observations included newly emerged leaves with typical, parallel veination and distorted leaves, as well as leaf pedicels and canes that had typical curved and twisted growth.

Remedial Spray:

| Material | Rate/100 gallons |
| --- | --- |
| GREEN THUMB 1-0-2 | 5 gallons |
| INTEGRITY CALCIUM | 4 quarts |
| SILWET L-77 | 3 ounces |
| BUD-SET | 12 ounces |

To prepare the composition for use, a spray tank was filled at least ¾ full with water and agitated before blending the above-described materials. The materials were added to the spray tank and blended together.

The composition was applied to the vines at a volume that delivers a fine mist (about 25-about 80 gallons per acre). Application of the composition to the vines was repeated which included at least 3 consecutive sprays at 5 day intervals and thereafter every 7-10 days until the vines recovered from the phytotoxicity.

Results
restoration of normal growth by the third spray;
no vine mortality;
new growth without distortion and twisting;
treated vines manifested enlarged and thicker leaves; and
no carryover of 2,4-D into successive seasonal growth.

Conclusions

The phytotoxicant-exposed vines were successfully treated for phytotoxicity according to the subject methods.

5. Drift from the Diphenyl Ether Herbicide GOAL onto Almond Trees

In this experiment, grapevines experiencing phytotoxicity from drift of the phytotoxicant GOAL were treated according to the subject invention.

Protocol

The protocol was initiated five days after drift contamination. Prior to commencement of the treatment protocol, observations general chlorosis and incipient shot-holing if foliage and trees appeared chlorotic and stunted.

Remedial Spray:

| Material | Rate/100 gallons |
| --- | --- |
| GREEN THUMB 1-0-2 | 5 gallons |
| INTEGRITY CALCIUM | 4 quarts |
| SILWET L-77 | 3 ounces |

To prepare the composition for use, a spray tank was filled at least ¾ full with water and agitated before blending the above-described materials. The materials were added to the spray tank and blended together.

The composition was applied to the trees at a volume that delivers a fine mist (about 25-about 80 gallons per acre). Application of the composition to the trees was repeated which included at least 3 consecutive sprays at 5 day intervals and thereafter every 7-10 days until the trees recovered from the phytotoxicity.

Results
restoration of normal growth by the second spray;
no limb or tree mortality;
new growth exceeds vigor and quality of unaffected, untreated trees; and
no carryover of GOAL into successive seasonal growth.

Conclusions

The phytotoxicant-exposed trees were successfully treated for phytotoxicity according to the subject methods.

B. Accidental Foliar Spray with a Toxicant 1. Accidental Spray with Glyphosate (ROUNDUP)

In this set of experiments, peaches and almonds experiencing phytotoxicity from accidental foliar spray of the phytotoxicant glyphosate (ROUNDUP) were treated according to the subject invention. The accidental spraying resulted from the use of an unmarked container of ROUNDUP for foliar spraying which was mistaken for a fungicide.

a. Accidental Spraying of ROUNDUP onto Peach Trees

Protocol

The protocol was initiated five days after the accidental foliar spraying. Prior to commencement of the treatment protocol, observations included new foliage initiating typical spindle shape with chlorosis, limbs exuding gum from buds and advanced stages of toxicity with the onset of defoliation.

Remedial Spray:

| Material | Rate/100 gallons |
|---|---|
| GREEN THUMB 1-0-2 | 5 gallons |
| INTEGRITY CALCIUM | 4 quarts |
| SILWET L-77 | 3 ounces |

To prepare the composition for use, a spray tank was filled at least ¾ full with water and agitated before blending the above-described materials. The materials were added to the spray tank and blended together.

The composition was applied to the trees at a volume that delivers a fine mist (about 25-about 80 gallons per acre). Application of the composition to the trees was repeated which included at least 3 consecutive sprays at 5 day intervals and thereafter every 7-10 days until the trees recovered from the phytotoxicity.

Results restoration of normal growth by the fourth spray;

occasional minor limb but no tree mortality;

no carryover of the phytotoxicant ROUNDUP into successive seasonal growth.

Conclusions

The phytotoxicant-exposed trees were successfully treated for phytotoxicity according to the subject methods.

b. Accidental Spraying of ROUNDUP onto Almond Trees

Protocol

The protocol was initiated five days after the accidental foliar spraying. Prior to commencement of the treatment protocol, observations included new growth initiating typical spindle leaf and chlorosis and occasional limbs with incipient gummosis.

Remedial Spray:

| Material | Rate/100 gallons |
|---|---|
| GREEN THUMB 1-0-2 | 5 gallons |
| INTEGRITY CALCIUM | 4 quarts |
| SILWET L-77 | 3 ounces |

To prepare the composition for use, a spray tank was filled at least ¾ full with water and agitated before blending the above-described materials. The materials were added to the spray tank and blended together.

The composition was applied to the trees at a volume that delivers a fine mist (about 25-about 80 gallons per acre). Application of the composition to the trees was repeated which included at least 3 consecutive sprays at 5 day intervals and thereafter every 7-10 days until the trees recovered from the phytotoxicity.

Results restoration of normal growth by the fourth spray;

no limb or tree mortality;

new growth volume and quality substantial with larger, thicker leaves; and no carryover of the phytotoxicant ROUNDUP into successive seasonal growth.

Conclusions

The phytotoxicant-exposed trees were successfully treated for phytotoxicity according to the subject methods.

2. Accidental Spray with Narrow Range Oil (A Low, Unsulfonated Residue Summer Spray Oil) Provided by Chevron, Inc.)

In this set of experiments, peaches and almonds experiencing phytotoxicity from accidental spraying of with a narrow range oil were treated according to the subject invention.

a. Accidental Spraying of Narrow Range Oil onto Peach Trees

Protocol

The protocol was initiated two days after the accidental spraying. The peach trees were previously sprayed with sulfur and the interaction of the sulfur and the oil formed sulfuric acid. Prior to commencement of the treatment protocol, observations included foliage having incipient chlorosis and defoliation and subtle to incipient gummosis.

Remedial Spray:

| Material | Rate/100 gallons |
|---|---|
| GREEN THUMB 1-0-2 | 5 gallons |
| INTEGRITY CALCIUM | 4 quarts |
| SILWET L-77 | 3 ounces |

To prepare the composition for use, a spray tank was filled at least ¾ full with water and agitated before blending the above-described materials. The materials were added to the spray tank and blended together.

The composition was applied to the trees at a volume that delivers a fine mist (about 25-about 80 gallons per acre). Application of the composition to the trees was repeated which included at least 3 consecutive sprays at 5 day intervals and thereafter every 7-10 days until the trees recovered from the phytotoxicity.

Results restoration of normal growth by the second spray;

minor defoliation with abundant, renewed foliage and shoot growth; and no deleterious effects on subsequent season cropping.

Conclusions

The phytotoxicant-exposed trees were successfully treated for phytotoxicity according to the subject methods.

b. Accidental Spraying of Narrow Range Oil onto Almond Trees

Protocol

The protocol was initiated three days after the accidental spraying. The almond trees were previously sprayed with the dicaroximide fungicide CAPTAN, forming a phytotoxic mixture. Prior to commencement of the treatment protocol, observations included foliage having incipient chlorosis and occasional defoliation.

Remedial Spray:

| Material | Rate/100 gallons |
|---|---|
| GREEN THUMB 1-0-2 | 5 gallons |
| INTEGRITY CALCIUM | 4 quarts |
| SILWET L-77 | 3 ounces |

To prepare the composition for use, a spray tank was filled at least ¾ full with water and agitated before blending the above-described materials. The materials were added to the spray tank and blended together.

The composition was applied to the trees at a volume that delivers a fine mist (about 25-about 80 gallons per acre). Application of the composition to the trees was repeated which included at least 3 consecutive sprays at 5 day intervals and thereafter every 7-10 days until the trees recovered from the phytotoxicity.

Results restoration of normal growth by the second spray;

no limb or tree mortality;

new growth volume and quality substantial with larger, thicker leaves; and no deleterious effects on successive seasonal growth and yields.

Conclusions

The phytotoxicant-exposed trees were successfully treated for phytotoxicity according to the subject methods.

c. Accidental Spraying of Narrow Range Oil onto Almond Trees

Protocol

The protocol was initiated three days after the accidental spraying. The almond trees were previously sprayed with the organosulfur miticide OMITE and the interaction of the OMITE and the oil formed a phytotoxic mixture. Prior to commencement of the treatment protocol, observations included foliage having incipient chlorosis and defoliation.

Remedial Spray:

| Material | Rate/100 gallons |
|---|---|
| GREEN THUMB 1-0-2 | 5 gallons |
| INTEGRITY CALCIUM | 4 quarts |
| SILWET L-77 | 3 ounces |

To prepare the composition for use, a spray tank was filled at least ¾ full with water and agitated before blending the above-described materials. The materials were added to the spray tank and blended together.

The composition was applied to the trees at a volume that delivers a fine mist (about 25-about 80 gallons per acre). Application of the composition to the trees was repeated which included at least 3 consecutive sprays at 5 day intervals and thereafter every 7-10 days until the trees recovered from the phytotoxicity.

Results restoration of normal growth by the second spray;

no limb or tree mortality;

new growth volume and quality substantial with larger, thicker leaves; and no deleterious effects on successive seasonal growth and yields.

Conclusions

The phytotoxicant-exposed trees were successfully treated for phytotoxicity according to the subject methods.

C. Planting onto Herbicide (And Other Chemical(s))-Contaminated Soil

1. Planting Turf onto Soil Contaminated with the Pyridazinone Herbicide SOLICAM

In this experiment, turf was planted into SOLICAM-contaminated soil and was experiencing phytotoxicity from the exposure to the herbicide SOLICAM. The turf was treated in accordance with the subject invention ten days prior to the time when the sod needed to be harvested.

Protocol

The protocol was initiated about three months after planting. Prior to commencement of the treatment protocol, observations included leaf blades typically bleached white and stunted.

Bioremediation:

| Material | Rate/acre |
|---|---|
| UAN-32 | 5 gallons |
| 10-34-0 | 1 gallon |
| water | 4 gallons |
| TILTH | 40 gallons |
| IOTA+ | 1 gallon |

Under agitation, the UAN-32, water 10-34-0 and TILTH were blended together. IOTA was added last. The mixture was injected into the sprinkler system for even distribution.

Remedial Spray:

| Material | Rate/100 gallons |
|---|---|
| GREEN THUMB 1-0-2 | 5 gallons |
| INTEGRITY CALCIUM | 4 quarts |
| SILWET L-77 | 3 ounces |
| BUD-SET | 12 ounces |

To prepare the composition for use, a spray tank was filled at least ¾ full with water and agitated before blending the above-described materials. The materials were added to the spray tank and blended together.

The composition was applied to the turf at a volume that delivers a fine mist (about 25-about 80 gallons per acre). Application of the composition to the turf was repeated which included at least 3 consecutive sprays at 3 day intervals and thereafter every 7-10 days until the turf recovered from the phytotoxicity.

Results restoration of normal growth by seventh day following initial treatment;

treated turf remediated to green coloration;

new growth green and leaf blades larger than before;

no turf mortality;

no carryover of SOLICAM into subsequent growth; and soil showed complete bioremediation of SOLICAM as demonstrated by bioassay that included seeding the soil with an indicator plant, Field Mustard, and observing the indicator plant for potential symptoms.

Conclusions

The phytotoxicant-exposed turf was successfully treated for phytotoxicity according to the subject methods. Furthermore, complete bioremediation of SOLICAM in the soil was achieved.

2. Soil Contaminated with the Combination Herbicide KROVAR (Which Includes DIURON (A Substituted Urea) and BROMACIL (A Substituted Uracil))

In this experiment, soil was contaminated with KROVAR. Strawberry vines were subsequently planted into the KROVAR-contaminated soil and were experiencing phytotoxicity from the exposure to the KROVAR. The ground in which the vines were planted was previously planted to citrus, a crop in which KROVAR was used for pre-emergence weed control. Chemical analysis of the soil prior to initiating the below-described protocol indicated BROMACIL at a concentration of 2 ppm and DIURON at a concentration of 12 ppm. Bioassay analysis of the soil indicated extremely high levels of KROVAR.

Protocol

The soil bioremediation protocol was initiated 2½ weeks before planting of the vines and the remedial spraying was initiated 3-5 days after planting of the vines. Prior to commencement of the treatment protocol, observations included no germination or growth of the indicator weed (field mustard).

Bioremediation:

| Material | Rate/acre |
| --- | --- |
| UAN-32 | 25 gallons |
| 10-34-0 | 5 gallon |
| water | 10 gallons |
| TILTH | 100 gallons |
| IOTA+ | 5 gallon |

Under agitation, the UAN-32, water 10-34-0 and TILTH were blended together. IOTA was added last. The mixture was injected into the sprinkler system for even distribution.

Remedial Spray:

| Material | Rate/100 gallons |
| --- | --- |
| GREEN THUMB 1-0-2 | 4 gallons |
| INTEGRITY CALCIUM | 3 quarts |
| SILWET L-77 | 3 ounces |
| BUD-SET | 12 ounces |

To prepare the composition for use, a spray tank was filled at least ¾ full with water and agitated before blending the above-described materials. The materials were added to the spray tank and blended together.

The composition was applied to the vines at a volume that delivers a fine mist (about 25-about 60 gallons per acre). Application of the composition to the vines was repeated regularly on a 7-10 day schedule throughout the growing season.

Results normal growth, free of KROVAR phytotoxicity was observed throughout the growing season; and treated soil showed complete remediation as demonstrated by bioassay that included seeding the soil with an indicator plant, Field Mustard, and observing the indicator plant for potential symptoms.

Conclusions

The phytotoxicant-exposed vines were successfully treated for phytotoxicity according to the subject methods. Furthermore, complete bioremediation of KROVAR in the soil was achieved.

3. Soil Contaminated with the Imidazolinone Herbicide ASSERT

In this experiment, soil was contaminated with ASSERT. Russet potatoes were subsequently planted into the ASSERT-contaminated soil and were experiencing phytotoxicity from the exposure to the ASSERT. ASSERT had been previously applied to a rotation crop (wheat) planted in the soil.

Protocol

The soil bioremediation protocol was initiated about 2 weeks before planting of the potato plants and the remedial spraying was initiated at the 3-5 leaf stage. Prior to commencement of the treatment protocol, bioassay analysis indicated the presence of levels of ASSERT in the soil that are phytotoxic to potato plants as demonstrated by bioassay that included seeding the soil with an indicator plant, Field Mustard, and observing the indicator plant for potential symptoms.

Soil Bioremediation:

| Material | Rate/acre |
| --- | --- |
| UAN-32 | 5 gallons |
| 10-34-0 | 1 gallon |
| water | 4 gallons |
| TILTH | 40 gallons |
| IOTA+ | 1 gallon |

Under agitation, the UAN-32, water 10-34-0 and TILTH were blended together. IOTA was added last. The mixture was injected into the sprinkler system for even distribution.

Remedial Spray:

| Material | Rate/100 gallons |
| --- | --- |
| GREEN THUMB 1-0-2 | 4 gallons |
| INTEGRITY CALCIUM | 4 quarts |
| SILWET L-77 | 3 ounces |
| BUD-SET | 12 ounces |

To prepare the composition for use, a spray tank was filled at least ¾ full with water and agitated before blending the above-described materials. The materials were added to the spray tank and blended together.

The composition was applied to the plants at a volume that delivers a fine mist (about 15-about 40 gallons per acre). Application of the composition to the plants was repeated at least 3 more times at 7 day intervals beginning with the 3-5 leaf stage.

Results no signs of ASSERT toxicity observed in the potato plants throughout the season;

treated soil showed complete bioremediation of the toxicant as demonstrated by bioassay that included seeding the soil with an indicator plant, Field Mustard, and observing the indicator plant for potential symptoms;

potato plant growth in an untreated control area manifested weak stand, stunted, chlorotic growth; and potato plant growth in treated, contaminated areas showed superior leaf size and green coloration relative to plants growing in an untreated, uncontaminated area.

Conclusions

The phytotoxicant-exposed plants were successfully treated for phytotoxicity according to the subject methods. Furthermore, complete remediation of the toxicant in the soil was achieved.

4. Soil Contaminated with Natural Toxins ("Allelopathic Toxins") from Previous Crop Shreddings In these experiments, soil was contaminated with allelopathic toxins. Almond trees and asters were subsequently planted into the contaminated soil and were experiencing phytotoxicity from the exposure to the allelopathic toxins. The contaminated soil was soil where sawdust from previous orchards shreddings had been stockpiled. Previous experience with plant growth in such soils has consistently has resulted in stunted, reduced growth quality. Fumigation of such soils has produced aggravation of the allelopathy through destruction of beneficial, degradative microflora.

a. Almond Trees Planted into the Allelopathic Toxin-Contaminated Soil

Protocol

The soil bioremediation protocol was initiated 2 weeks before planting of the almond trees into the soil and the remedial spraying was initiated at the 3-5 true leaf stage.

Soil Bioremediation:

| Material | Rate/acre |
|---|---|
| UAN-32 | 20 gallons |
| 10-34-0 | 5 gallon |
| water | 10 gallons |
| TILTH | 40 gallons |
| IOTA+ | 3 gallon |

Under agitation, the UAN-32, water 10-34-0 and TILTH were blended together. IOTA was added last. The mixture was injected into the sprinkler system for even distribution.

Remedial Spray:

| Material | Rate/100 gallons |
|---|---|
| GREEN THUMB 1-0-2 | 4 gallons |
| INTEGRITY CALCIUM | 3 quarts |
| SILWET L-77 | 3 ounces |
| BUD-SET | 12 ounces |

To prepare the composition for use, a spray tank was filled at least ¾ full with water and agitated before blending the above-described materials. The materials were added to the spray tank and blended together.

The composition was applied to the trees at a volume that delivers a fine mist (about 25-about 60 gallons per acre). Application of the composition to the trees was repeated regularly on a 10-14 day schedule throughout the growing season.

Results

- normal growth, free of allelopathic phytotoxicity was observed throughout the growing season;
- treated soil tested through bioassays indicated complete bioremediation;
- treated soil showed significant reductions in soil-borne pathogens: *Rhizoctonia solani, Verticillium dahliae, Fusarium* spp., *Phytophthora* spp.;
- treated soil shoed significant reductions in plant-parasitic nematodes species and a concomitant increase in beneficial, free-living nematodes, tardigrades and mites; and
- host almond trees in treated areas showed larger stature, girth and lateral branching.

Conclusions

The phytotoxicant-exposed trees were successfully treated for phytotoxicity and the contaminated soil was successfully treated according to the subject methods. Furthermore, complete remediation of the toxicant in the soil was achieved.

b. Asters Planted into the Allelopathic Toxin-Contaminated Soil

The treatment protocol was initiated 1 week following the removal of the previously planted aster crops. Asters are known for allelopathic hindrances to subsequent plantings. Typically, the opportunity for successful germination and growth of a subsequent crop only occurs following 1-2 years fallow ground.

Protocol

The soil bioremediation protocol was initiated 10 days before planting and the remedial spraying was initiated at the 3-5 true leaf stage.

Soil Bioremediation:

| Material | Rate/acre |
|---|---|
| UAN-32 | 15 gallons |
| 10-34-0 | 5 gallon |
| water | 10 gallons |
| TILTH | 50 gallons |
| IOTA+ | 3 gallon |

Under agitation, the UAN-32, water 10-34-0 and TILTH were blended together. IOTA was added last. The mixture was injected into the sprinkler system for even distribution.

Remedial Spray:

| Material | Rate/100 gallons |
|---|---|
| GREEN THUMB 1-0-2 | 4 gallons |
| INTEGRITY CALCIUM | 3 quarts |
| SILWET L-77 | 3 ounces |
| BUD-SET | 12 ounces |

To prepare the composition for use, a spray tank was filled at least ¾ full with water and agitated before blending the above-described materials. The materials were added to the spray tank and blended together.

The composition was applied to the asters at a volume that delivers a fine mist (about 25-about 60 gallons per acre). Application of the composition to the asters was repeated regularly on a 10-14 day schedule throughout the growing season.

Results

- normal growth, free of allelopathic phytotoxicity was observed throughout the growing season;
- treated soil tested through bioassays indicated complete bioremediation;
- treated soil showed significant reductions in soil-borne pathogens: *Rhizoctonia solani, Verticillium dahliae, Fusarium* spp., *Phytophthora* spp.;
- treated soil showed significant reductions in plant-parasitic nematodes species and a concomitant increase in beneficial, free-living nematodes, tardigrades and mites; and
- host aster plants in treated areas showed larger stature, girth and lateral branching.

Conclusions

The phytotoxicant-exposed plants were successfully treated for phytotoxicity and the contaminated soil was successfully treated according to the subject methods. Furthermore, complete remediation of the toxicant in the soil was achieved.

It is evident from the above results and discussion that the subject invention provides novel methods of treating a plant exposed or at least suspected of being expose to a phytotoxicant. The compositions employed in the practice of the subject methods can provide for significant improvement in terms of at least reduced phytotoxicity, e.g., improved plant health and the like relative to phytotoxicity observed prior to application of the subject compositions to a phytotoxicant-exposed plant, and are easy to prepare and use. The versatility of the subject methods enables the effective treatment of a wide variety of phytotoxicant-exposed plants, at least reduces the toxic effects of a wide variety of phytotoxicants and enables the application of a phytotoxicant-fighting composition to a plant in need thereof using a wide variety of methods. As such, the subject invention is a significant advance in the art.

All publications and patent applications mentioned in this specification are herein incorporated by reference to the same extent as if each individual publication or patent application was specifically and individually indicated to be incorporated by reference.

The invention now being fully described, it will be apparent to one of skill in the art that many changes and modifications can be made thereto without departing from the spirit and scope of the appended claims.

What is claimed is:

1. A method of treating a plant exposed to a phytotoxicant, said method comprising:
    (a) identifying a plant exposed to a phytotoxicant by direct exposure of foliage of said plant to said phytotoxicant; and
    (b) applying a phytotoxicity-reducing amount of an assimilable carbon-skeleton energy component-comprising composition to said identified plant to at least ameliorate the symptoms associated with said exposure to the phytotoxicant.

2. The method of claim 1, wherein said applying comprises applying said assimilable carbon-skeleton energy component-comprising composition to the soil associated with said plant.

3. The method of claim 2, wherein said assimilable carbon-skeleton energy component-comprising composition is applied to said soil by adding said composition to water used to irrigate said plant.

4. The method of claim 1, wherein said applying comprises applying said assimilable carbon-skeleton energy component-comprising composition to the foliage of said plant.

5. The method of claim 1, wherein said assimilable carbon-skeleton energy component-comprising composition is applied at a rate of about 15 to about 100 gallons/acre.

6. The method of claim 1, wherein said assimilable carbon-skeleton energy component-comprising composition is applied to said plant about 1 hour to about 21 days after said plant is at least suspected of being exposed to said phytotoxicant.

7. The method of claim 6, wherein said method comprises repeating said applying step at least one additional time.

8. The method of claim 7, wherein said applying is repeated at least one additional time within a period of time ranging from about 24 hours to about 21 days following the initial applying step.

9. The method of claim 8, wherein said applying is repeated at least about 2 to about 5 times at intervals ranging from about every 2 days to about every 20 days following the initial applying step.

10. The method of claim 1, wherein said exposure is accidental.

11. The method of claim 10, wherein said accidental exposure is a result of accidental drift of said phytotoxicant.

12. The method of claim 1, wherein said exposure is by purposeful foliar spray.

13. The method of claim 1, wherein said assimilable carbon-skeleton energy component-comprising composition further comprises a macronutrient component.

14. The method of claim 1, wherein said assimilable carbon-skeleton energy component-comprising composition further comprises a micronutrient component.

15. The method of claim 1, wherein said assimilable carbon-skeleton energy component-comprising composition further comprises a vitamin/cofactor component.

16. The method of claim 1, wherein said assimilable carbon-skeleton energy component-comprising composition further comprises a complexing agent.

17. The method of claim 1, wherein said assimilable carbon-skeleton energy component-comprising composition further comprises at least one species of microbe.

18. The method of claim 17, wherein said at least one species of microbe is capable of antagonizing at least one plant pathogen.

19. The method of claim 1, wherein said method at least results in a reduction of said phytotoxicity.

20. The method of claim 1, wherein said method further comprises, prior to applying said assimilable carbon-skeleton energy component-comprising composition to said plant, determining the source of said phytotoxicant.

21. The method of claim 1, wherein said phytotoxicant is a pesticide.

22. A kit comprising:
    (a) an assimilable carbon-skeleton energy component-comprising composition, and
    (b) instructions for using said assimilable carbon-skeleton energy component-comprising composition according to the method of claim 1.

* * * * *